US009662291B2

(12) United States Patent
Johnson et al.

(10) Patent No.: US 9,662,291 B2
(45) Date of Patent: *May 30, 2017

(54) METHOD OF ACHIEVING IMPROVED HAIR FEEL

(71) Applicant: The Procter & Gamble Company, Cincinnati, OH (US)

(72) Inventors: Eric Scott Johnson, Hamilton, OH (US); James Anthony Staudigel, Loveland, OH (US); Sean Michael Renock, Loveland, OH (US); Beth Ann Schubert, Maineville, OH (US); Mark William Hamersky, Indian Springs, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/004,284

(22) Filed: Jan. 22, 2016

(65) Prior Publication Data
US 2016/0143835 A1 May 26, 2016

Related U.S. Application Data

(63) Continuation of application No. 13/646,272, filed on Oct. 5, 2012, now Pat. No. 9,272,164.

(60) Provisional application No. 61/544,750, filed on Oct. 7, 2011.

(51) Int. Cl.
| A61Q 5/12 | (2006.01) |
| A61K 8/27 | (2006.01) |
| A61K 8/73 | (2006.01) |
| A61K 8/81 | (2006.01) |
| A61K 8/02 | (2006.01) |
| A61K 8/44 | (2006.01) |
| A61K 8/46 | (2006.01) |
| A61K 8/58 | (2006.01) |
| A61K 8/891 | (2006.01) |
| A61Q 5/00 | (2006.01) |

(52) U.S. Cl.
CPC ............ *A61K 8/737* (2013.01); *A61K 8/0241* (2013.01); *A61K 8/27* (2013.01); *A61K 8/442* (2013.01); *A61K 8/463* (2013.01); *A61K 8/58* (2013.01); *A61K 8/8158* (2013.01); *A61K 8/891* (2013.01); *A61Q 5/006* (2013.01); *A61Q 5/12* (2013.01); A61K 2800/412 (2013.01); A61K 2800/49 (2013.01); A61K 2800/5426 (2013.01); A61K 2800/594 (2013.01); A61K 2800/74 (2013.01)

(58) Field of Classification Search
None
See application file for complete search history.

(56) References Cited

U.S. PATENT DOCUMENTS

| 2,809,971 | A | 10/1957 | Bernstein et al. |
| 3,236,733 | A | 2/1966 | Karsten et al. |
| 3,753,196 | A | 8/1973 | Kurtz et al. |
| 3,761,418 | A | 9/1973 | Parran |
| 4,323,683 | A | 4/1982 | Bolich, Jr. et al. |
| 4,345,080 | A | 8/1982 | Bolich, Jr. |
| 4,379,753 | A | 4/1983 | Bolich, Jr. |
| 4,470,982 | A | 9/1984 | Winkler |
| 5,104,646 | A | 4/1992 | Bolich, Jr. et al. |
| 5,106,609 | A | 4/1992 | Bolich, Jr. et al. |
| 5,723,112 | A | 3/1998 | Bowser et al. |
| 5,925,615 | A * | 7/1999 | Kern ..................... A61K 8/97 424/74 |
| 8,491,877 | B2 | 7/2013 | Schwartz |
| 2003/0176303 | A1 | 9/2003 | Niemiec et al. |
| 2004/0157755 | A1 | 8/2004 | Niemiec et al. |
| 2007/0207109 | A1 | 9/2007 | Peffly |
| 2007/0276087 | A1 | 11/2007 | Paul |
| 2008/0206179 | A1 | 8/2008 | Peffly et al. |
| 2008/0206355 | A1 | 8/2008 | Schwartz et al. |

(Continued)

FOREIGN PATENT DOCUMENTS

| CN | 101904908 A | 12/2010 |
| EP | 0074819 A | 3/1983 |
| EP | 0136914 A | 4/1985 |

(Continued)

OTHER PUBLICATIONS

Engmann, J. et el. "Squeeze Flow Theory and Applications to Rheometry: A Review" J. of Non-Newtonian Fluid Mechanics, 132 (2005) 1-27.
Lepilleur, Carole, et al. "Use of Statistical modeling to predict the effect of formulation composition on coacervation, silicone deposition, and conditioning sensory performance of Cationic Cassia Polymers" J. Cosmet Sci., 62, 161-177.
Morioka, H., Tagaya, H., Karasu, M, Kadokawa, J, Chiba, K "Effects of Zinc on the New Preparation Method of Hydroxy Double Salts"Inorg. Chem. 1999, 38, 4211-6.
International Search Report PCT/US2012/058990; Mailing Date Nov. 7, 2013; 13 pages.

Primary Examiner — Jennifer A Berrios
(74) Attorney, Agent, or Firm — Linda M. Sivik

(57) ABSTRACT

A method of achieving improved hair feel. The method comprises applying to hair a composition comprising: (a) a specific cationic guar polymer; (b) a specific cationic copolymer; (c) an anti-dandruff active; (d) a cosmetically acceptable carrier; (e) a surfactant; wherein the weight ratio of (a):(b) is from about 1000:1 to about 3.5:1; and wherein the sum of (a)+(b) is an amount of from about 0.0001% to about 0.7%, by total weight of the composition. The composition forms coacervate particles upon dilution of the composition with water and the coacervate particles have a squeeze flow viscosity of from about 1 cP to about 100 cP. The percentage of coacervate particles with a floc size of greater than about 20 micron is from about 1% to about 60% and the on-scalp deposition of the anti-dandruff active is at least about 1 microgram/$cm^2$.

17 Claims, 1 Drawing Sheet

(56) References Cited

U.S. PATENT DOCUMENTS

| | | | | |
|---|---|---|---|---|
| 2009/0176674 | A1* | 7/2009 | Peffly | A61K 8/27 510/121 |
| 2011/0002868 | A1* | 1/2011 | Bierganns | A61K 8/737 424/70.13 |

FOREIGN PATENT DOCUMENTS

| | | | |
|---|---|---|---|
| EP | 1080714 | A2 | 3/2001 |
| EP | 1437121 | A1 | 7/2004 |
| WO | 9986886 | A | 6/1998 |
| WO | 2010080167 | A2 | 7/2010 |
| WO | 2013050241 | A1 | 4/2013 |

* cited by examiner

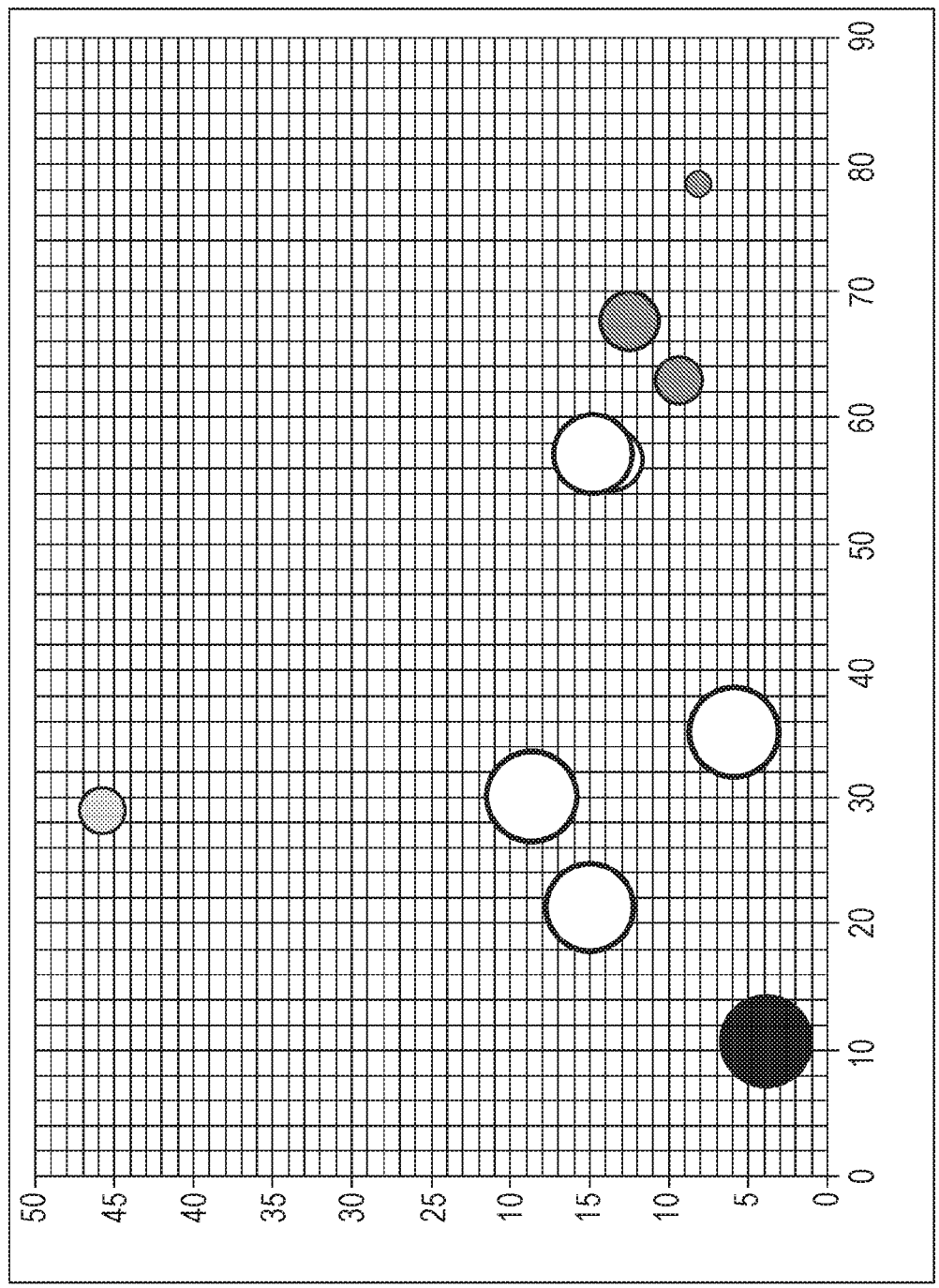

US 9,662,291 B2

METHOD OF ACHIEVING IMPROVED HAIR FEEL

FIELD OF THE INVENTION

A method of achieving improved hair feel, comprising applying to hair a composition comprising: (a) a specific cationic guar polymer; (b) a specific cationic copolymer; (c) an anti-dandruff active; (d) a cosmetically acceptable carrier; (e) a surfactant; wherein the weight ratio of (a):(b) is from about 1000:1 to about 3.5:1; and wherein the sum of (a)+(b) is an amount of from about 0.0001% to about 0.7%, by total weight of the composition; wherein the composition forms coacervate particles upon dilution of the composition with water; and wherein the coacervate particles have a squeeze flow viscosity of from about 1 cP to about 100 cP; and wherein the percentage of coacervate particles with a floc size of greater than about 20 micron is from about 1% to about 60%; and wherein the on-scalp deposition of the anti-dandruff active is at least about 1 microgram/cm$^2$.

BACKGROUND OF THE INVENTION

Conditioning shampoos or "2 in 1" hair products comprising a detersive surfactant and hair conditioning agents are known. These personal care compositions typically comprise an anionic detersive surfactant in combination with a conditioning agent such as a silicone, hydrocarbon oil, fatty esters etc. These products have become more popular among consumers as a means of conveniently obtaining hair conditioning and cleansing performance from a single product.

Many conditioning personal care compositions, however, do not provide sufficient deposition of conditioning agents onto hair or skin during the application process and if deposition is possible, it is only possible in formulations with relatively low levels of anionic surfactant. Without adequate deposition, large proportions of conditioning agent are rinsed away during the application process and therefore provide little or no conditioning benefit. Without sufficient deposition of the conditioning agent on the hair or skin, relatively high levels of conditioning agents may be needed. Such high levels of a conditioning agent, however, can increase raw material costs, reduce lathering, and present product stability concerns. Additionally, limitations on total anionic surfactant in order to form coacervate can limit the lather potential of a composition, or result in the need for higher levels of less cost effective amphoteric surfactants in order to achieve good lather.

One known method for improving deposition of a hair conditioning agent onto hair involves the use of specific cationic deposition polymers. These polymers may be synthetic, but are most commonly natural cellulosic or guar polymers that have been modified with cationic substituents.

The formation of coacervate upon dilution of the cleansing composition with water is important to improving deposition of various conditioning actives, especially those that have small droplet sizes (i.e., ≤2 microns). In order to form coacervate, cleansing compositions comprising typical cationic polymers tend to be significantly limited in total anion concentrations, in order to achieve adequate levels of coacervate upon dilution, but this will limit the volume of lather that can be achieved with a particular cleansing composition. Thus, for cost effective, high lathering, coacervate-forming compositions, it is desirable to use a cationic polymer that can form coacervate in the presence of high levels of anionic surfactant. Another complexity arises when the composition comprises an anti-dandruff active which also needs to be deposited on the scalp in an efficacious deposition amount and quality. However, excellent deposition amount and quality of anti-dandruff actives, for example by utilizing high levels of cationic polymers and those with higher charge density, is often associated with a hair conditioning feel that many consumers find unacceptable.

Consequently, needs exist for a conditioning anti-dandruff composition that provides excellent anti-dandruff deposition performance without a hair conditioning and hair feel trade-off.

SUMMARY OF THE INVENTION

According to a first aspect, the present invention relates to a method of achieving improved hair feel, comprising applying to hair a composition comprising:
(a) a cationic guar polymer, wherein the cationic guar polymer has a weight average molecular weight of less than about 1 million g/mol, and wherein the cationic guar polymer has a charge density of from about 0.1 meq/g to about 2.5 meq/g;
(b) a cationic copolymer of an acrylamide monomer and a cationic monomer, wherein the copolymer has a charge density of from about 1.0 meq/g to about 3.0 meq/g;
(c) an anti-dandruff active;
(d) a cosmetically acceptable carrier;
(e) a surfactant;
wherein the weight ratio of (a):(b) is from about 1000:1 to about 3.5:1;
and wherein the sum of (a)+(b) is an amount of from about 0.0001% to about 0.7%, by total weight of the composition;
wherein the composition forms coacervate particles upon dilution of the composition with water;
and wherein the coacervate particles have a squeeze flow viscosity of from about 1 cP to about 100 cP;
and wherein the percentage of coacervate particles with a floc size of greater than about 20 micron is from about 1% to about 60%;
and wherein the on-scalp deposition of the anti-dandruff active is at least about 1 microgram/cm$^2$.

According to a second aspect, the present invention relates to a hair conditioning composition comprising:
(a) a cationic guar polymer, wherein the cationic guar polymer has a weight average molecular weight of less than about 1 million g/mol, and wherein the cationic guar polymer has a charge density of from about 0.1 meq/g to about 2.5 meq/g;
(b) a cationic copolymer of an acrylamide monomer and a cationic monomer, wherein the copolymer has a charge density of from about 1.0 meq/g to about 3.0 meq/g;
(c) an anti-dandruff active;
(d) a cosmetically acceptable carrier;
(e) a surfactant;
wherein the weight ratio of (a):(b) is from about 1000:1 to about 3.5:1;
and wherein the sum of (a)+(b) is an amount of from about 0.0001% to about 0.7%, by total weight of the composition.

According to a third aspect, the present invention relates to the use of the composition, according to the second aspect, for treating hair.

According to a fourth aspect, the present invention relates to a kit comprising:

(a) application instructions comprising the method according to the first aspect; and
(b) a composition.

BRIEF DESCRIPTION OF THE DRAWINGS

The FIGURE : Axis X: Coacervate squeeze flow viscosity in centipoise at 100 s$^{-1}$. Axis Y: percentage of coacervate particles with a floc size of greater than about 20 microns. Circle size corresponds to mean consumer acceptance rating (larger size equals higher acceptance rating). Circles with white fill represent compositions with coacervate particle properties that result in a mean consumer acceptance rating of 60 or higher, fall within the within the ratio of (a):(b) of about 1000:1 to about 3.5:1, have a sum of (a)+(b) less than 0.7%, and have an on-scalp anti-dandruff active deposition of greater than 1 microgram/cm$^2$. Circles with light grey fill represent compositions that exceed "(a)+(b) is less than 0.7%". Circles with dark grey and black fill represent compositions that are outside the ratio of (a):(b) of 1000:1 to 3.5:1.

DETAILED DESCRIPTION OF THE INVENTION

All percentages are by weight of the total composition, unless stated otherwise. All ratios are weight ratios, unless specifically stated otherwise. All ranges are inclusive and combinable. The number of significant digits conveys neither a limitation on the indicated amounts nor on the accuracy of the measurements. The term "molecular weight" or "M.Wt." as used herein refers to the weight average molecular weight unless otherwise stated. "QS" means sufficient quantity for 100%.

All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

Herein, "comprising" means that other steps and other ingredients which do not affect the end result can be added. This term encompasses the terms "consisting of" and "consisting essentially of". The compositions, methods, uses, kits, and processes of the present invention can comprise, consist of, and consist essentially of the elements and limitations of the invention described herein, as well as any of the additional or optional ingredients, components, steps, or limitations described herein.

The term "substantially free from" or "substantially free of" as used herein means less than about 1%, or less than about 0.8%, or less than about 0.5%, or less than about 0.3%, or about 0%, by total weight of the composition.

"Hair," as used herein, means mammalian hair including scalp hair, facial hair and body hair, particularly on hair on the human head and scalp.

"Cosmetically acceptable," as used herein, means that the compositions, formulations or components described are suitable for use in contact with human keratinous tissue without undue toxicity, incompatibility, instability, allergic response, and the like. All compositions described herein which have the purpose of being directly applied to keratinous tissue are limited to those being cosmetically acceptable.

"Derivatives," as used herein, includes but is not limited to, amide, ether, ester, amino, carboxyl, acetyl, acid, salt and/or alcohol derivatives of a given compound.

"Polymer," as used herein, means a chemical formed from the polymerisation of two or more monomers. The term "polymer" as used herein shall include all materials made by the polymerisation of monomers as well as natural polymers. Polymers made from only one type of monomer are called homopolymers. A polymer comprises at least two monomers. Polymers made from two or more different types of monomers are called copolymers. The distribution of the different monomers can be calculated statistically or blockwise—both possibilities are suitable for the present invention. Except if stated otherwise, the term "polymer" used herein includes any type of polymer including homopolymers and copolymers.

"Kit," as used herein, means a packaging unit comprising a plurality of components. An example of a kit is, for example, a first composition and a separately packaged second composition. Another kit may comprise a first composition and an energy delivery device. A different kit may comprise three different types of separately packaged composition and a hair styling implement. A further kit may comprise application instructions comprising a method and a composition/formulation.

The term "coacervate" as used herein, means the complex which forms between surfactant and polymer that may either be soluble or insoluble in the neat composition, typically forming an insoluble complex in the neat composition, and which may become less soluble upon dilution and thus yielding an increase in its level of phase separation or precipitate in solution.

The term "floc" as used herein, means localized clusters of agglomerated, insoluble coacervate, which may comprise polymer, surfactant, water and dispersed phases present in the composition such as anti-dandruff active and silicone emulsion. Any floc size disclosed herein is obtained using the Lasentec FBRM Method, which is described below.

The term "isotropic" as used herein, means a particular phase structure of coacervate wherein the structure is "identical along any three orthogonal directions in space, and is therefore dark or 'nonbirefringent' when viewed between crossed polarized light. (One direction is 'orthogonal' to another if the vector component of the first, in the direction of the second, is zero.) (Laughlin, R. G. (1994). "The Aqueous Phase Behavior of Surfactants," 182, 8.2).

The term "charge density" as used herein, means the ratio of the number of positive charges on a monomeric unit (of which a polymer is comprised) to the M.Wt. of said monomeric unit. The charge density multiplied by the polymer M.Wt. determines the number of positively charged sites on a given polymer chain. For cationic guars, charge density is measured using standard elemental analysis of percentage nitrogen known to one skilled in the art. This value of percentage nitrogen, corrected for total protein analysis, can then be used to calculate the number or equivalence of positive charges per gram of polymer. For the cationic copolymers, the charge density is a function of the monomers used in the synthesis. Standard NMR techniques know to one skilled in the art would be used to confirm that ratio of cationic and non-ionic monomers in the polymer. This would then be used to calculate the number or equivalence of positive charger per gram of polymer. Once these values are know, the charge density is reported in milliequivalence (meq) per gram of cationic polymer.

The term "(meth)acrylamide" as used herein means methylacrylamide or acrylamide. The term "(meth)acrylic acid" as used herein means acrylic acid or methacrylic acid.

It has been surprisingly found that, by formulating specific levels and ratios of specific cationic guar polymers and specific cationic copolymers of acrylamide monomers and cationic monomers, anti-dandruff active deposition can be improved with minimal or no consumer unacceptance of hair conditioning and hair feel.

Without being bound by theory, the inventors have found that a lower level of the cationic copolymer is needed versus the cationic guar polymers, in order to provide improved consumer acceptance of hair conditioning and hair feel and yet also excellent on-scalp anti-dandruff active deposition—such excellent on-scalp anti-dandruff active deposition correlating with the efficacy of the anti-dandruff active to combat dandruff. Cationic guars produce a coacervate with very desirable properties of coacervate floc size and coacervate rheology, which are very desirable due to the correlation of these properties with consumer acceptance of the resulting hair conditioning and hair feel. Certain cationic guars provide an acceptable consumer hair feel, but can be inefficient at depositing anti-dandruff actives. It has been shown that by increasing the M.Wt. of the cationic guar, more efficient anti-dandruff on-scalp deposition can be achieved, but this also results in a larger coacervate floc size. The large coacervate floc, when applied to hair, becomes trapped in the hair, which in turn results in a less accepted hair feel. Cationic copolymers, however, produce a coacervate that is very efficient at depositing anti-dandruff actives onto the scalp, but results in coacervate properties of floc size and rheology that make hair feel unacceptable to consumers. By providing a composition comprising a specific cationic guar and a specific cationic copolymer at a ratio and amount as defined herein, it has been surprisingly found that both the consumer desired benefits provided by the lower M.Wt. cationic guars and the enhanced deposition of the cationic copolymers can be achieved in a single composition while still preserving the high consumer acceptance of the hair conditioning performance and hair feel.

The features of the method according to the first aspect, as well as the other aspects and other relevant components, are described in detail hereinafter. All components of the composition described herein should be physically and chemically compatible with the essential components described herein, and should not otherwise unduly impair product stability, aesthetics or performance.

The composition comprises (a) a cationic guar polymer, wherein the cationic guar polymer has a weight average M.Wt. of less than about 1 million g/mol, and wherein the cationic guar polymer has a charge density of from about 0.1 meq/g to about 2.5 meq/g. Furthermore, the sum of (a)+(b) is an amount of from about 0.0001% to about 0.7%, by total weight of the composition. Cationic guar polymers are cationically substituted galactomannan (guar) gum derivatives. Guar gum for use in preparing these guar gum derivatives is typically obtained as a naturally occurring material from the seeds of the guar plant. The guar molecule itself is a straight chain mannan, which is branched at regular intervals with single membered galactose units on alternative mannose units. The mannose units are linked to each other by means of β(1-4) glycosidic linkages. The galactose branching arises by way of an α(1-6) linkage. Cationic derivatives of the guar gums are obtained by reaction between the hydroxyl groups of the polygalactomannan and reactive quaternary ammonium compounds. The degree of substitution of the cationic groups onto the guar structure must be sufficient to provide the requisite cationic charge density described above.

In an embodiment, the cationic guar polymer has a weight average M.Wt. of less than 900 thousand g/mol, or from about 150 thousand to about 800 thousand g/mol, or from about 200 thousand to about 700 thousand g/mol, or from about 300 thousand to about 700 thousand g/mol, or from about 400 thousand to about 600 thousand g/mol.

In an embodiment, the composition comprises from about 0.01% to about 0.7%, or from about 0.04% to about 0.55%, or from about 0.08% to about 0.5%, or from about 0.16% to about 0.5%, or from about 0.2% to about 0.5%, or from about 0.3% to about 0.5%, or from about 0.4% to about 0.5%, of cationic guar polymer (a), by total weight of the composition.

The cationic guar polymer may be formed from quaternary ammonium compounds. In an embodiment, the quaternary ammonium compounds for forming the cationic guar polymer conform to the general formula:

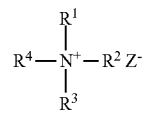

wherein where $R^1$, $R^2$ and $R^3$ are methyl or ethyl groups; $R^4$ is either an epoxyalkyl group of the general formula:

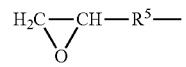

or $R^4$ is a halohydrin group of the general formula:

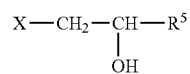

wherein $R^5$ is a $C_1$ to $C_3$ alkylene; X is chlorine or bromine, and Z is an anion such as Cl—, Br—, I— or $HSO_4$—.

In an embodiment, the cationic guar polymer conforms to the general formula:

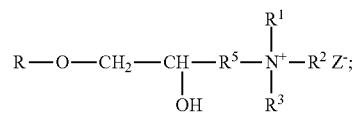

wherein R is guar gum; and wherein $R^1$, $R^2$, $R^3$ and $R^5$ are hydrocarbons comprising 1 to 6 carbon atoms; and wherein Z is a halogen. In an embodiment, the cationic guar polymer conforms to Formula G:

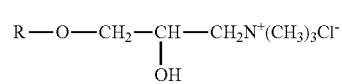

Formula G

Suitable cationic guar polymers include cationic guar gum derivatives, such as guar hydroxypropyltrimonium chloride. In an embodiment, the cationic guar polymer is a guar hydroxypropyltrimonium chloride. Specific examples of guar hydroxypropyltrimonium chlorides include the Jaguar® series commercially available from Rhone-Poulenc Incorporated, for example Jaguar® C-500, commercially available from Rhodia. Jaguar® C-500 has a charge density of 0.8 meq/g and a M.Wt. of 500,000 g/mole. Another guar hydroxypropyltrimonium chloride with a charge density of 1.1 meq/g and a M.Wt. of 500,000 g/mole is available from Ashland. A further guar hydroxypropyltrimonium chloride with a charge density of 1.5 meq/g and a M.Wt. of 500,000 g/mole is available from Ashland.

Jaguar® C-17 is not suitable as the cationic guar polymer (a) of the present invention. Jaguar® C-17 conforms to Formula G and has a cationic charge density of about 0.6 meq/g and a M.Wt. of about 2.2 million g/mol and is available from Rhodia Company. Jaguar® C 13S is also not suitable as the cationic guar polymer (a) of the present invention. Jaguar® C 13S conforms to Formula G and has a M.Wt. of 2.2 million g/mol and a cationic charge density of 0.8 meq/g (available from Rhodia Company). In an embodiment, the present invention is substantially free of Jaguar® C-17 and/or Jaguar® C 13S.

Other suitable polymers include: Hi-Care 1000, which has a charge density of 0.7 meq/g and a M.Wt. of 600,000 g/mole and is available from Rhodia; N-Hance 3269 and N-Hance 3270, which have a charge density of 0.7 meq/g and a M.Wt. of 425,000 g/mole and is available from Ashland; AquaCat CG518 has a charge density of 0.9 meq/g and a M.Wt. of 50,000 g/mole and is available from Ashland.

The composition comprises (b) a cationic copolymer of an acrylamide monomer and a cationic monomer, wherein the copolymer has a charge density of from about 1.0 meq/g to about 3.0 meq/g. Furthermore, the sum of (a)+(b) is an amount of from about 0.0001% to about 0.7%, by total weight of the composition. In an embodiment, the cationic copolymer is a synthetic cationic copolymer of acrylamide monomers and cationic monomers.

In an embodiment, the cationic copolymer comprises:
(i) an acrylamide monomer of the following Formula AM:

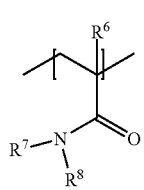

Formula AM where $R^6$ is H or $C_{1-4}$ alkyl; and $R^7$ and $R^8$ are independently selected from the group consisting of H, $C_{1-4}$ alkyl, $CH_2OCH_3$, $CH_2OCH_2CH(CH_3)_2$, and phenyl, or together are $C_{3-6}$cycloalkyl; and (ii) a cationic monomer conforming to Formula CM:

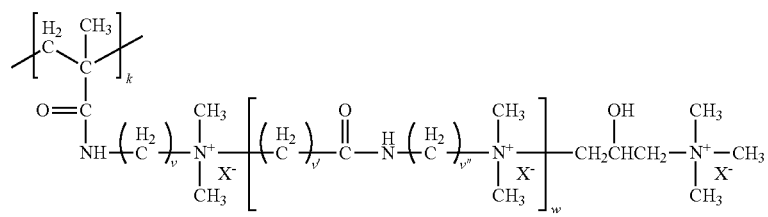

Formula CM where k=1, each of v, v', and v" is independently an integer of from 1 to 6, w is zero or an integer of from 1 to 10, and $X^-$ is an anion.

In an embodiment, cationic monomer conforming to Formula CM and where k=1, v=3 and w=0, z=1 and $X^-$ is $Cl^-$ to form the following structure:

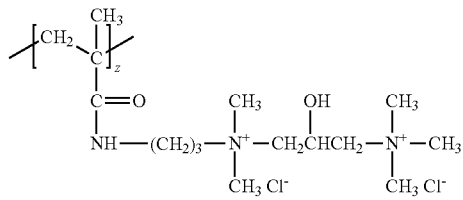

The above structure may be referred to as diquat. In another embodiment, the cationic monomer conforms to Formula CM and wherein v and v" are each 3, v'=1, w=1, y=1 and $X^-$ is $Cl^-$, such as:

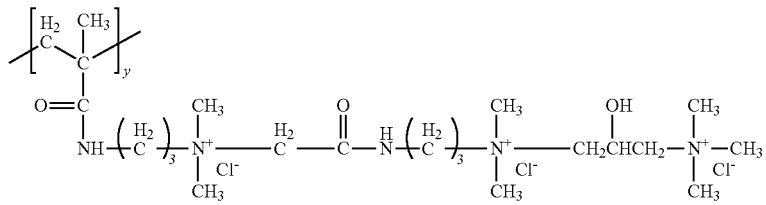

The above structure may be referred to as triquat.

In an embodiment, the acrylamide monomer is either acrylamide or methacrylamide.

In an embodiment, the cationic copolymer (b) is AM:TRIQUAT which is a copolymer of acrylamide and 1,3-Propanediaminium,N-[2-[[[dimethyl[3-[(2-methyl-1-oxo-2-propenyl)amino]propyl]ammonio]acetyl]amino]ethyl]2-hydroxy-N,N,N',N',N'-pentamethyl-, trichloride. AM:TRIQUAT is also known as polyquaternium-76 (PQ76). AM:TRIQUAT may have a charge density of 1.6 meq/g and a M.Wt. of 1.1 million g/mol.

In an alternative embodiment, the cationic copolymer is of an acrylamide monomer and a cationic monomer, wherein the cationic monomer is selected from the group consisting of: dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide; ethylenimine, vinylamine, 2-vinylpyridine, 4-vinylpyridine; trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, and mixtures thereof.

In an embodiment, the cationic copolymer comprises a cationic monomer selected from the group consisting of: cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, and mixtures thereof.

In an embodiment, the cationic copolymer is water-soluble. In an embodiment, the cationic copolymer is formed from (1) copolymers of (meth)acrylamide and cationic monomers based on (meth)acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. Monomers based on cationic (meth)acrylic acid esters may be cationized esters of the (meth)acrylic acid containing a quaternized N atom. In an embodiment, cationized esters of the (meth)acrylic acid containing a quaternized N atom are quaternized dialkylaminoalkyl (meth)acrylates with C1 to C3 in the alkyl and alkylene groups. In an embodiment, the cationized esters of the (meth)acrylic acid containing a quaternized N atom are selected from the group consisting of ammonium salts of dimethylaminomethyl (meth)acrylate, dimethylaminoethyl (meth)acrylate, dimethylaminopropyl (meth)acrylate, diethylaminomethyl (meth)acrylate, diethylaminoethyl (meth)acrylate; and diethylaminopropyl (meth)acrylate quaternized with methyl chloride. In an embodiment, the cationized esters of the (meth)acrylic acid containing a quaternized N atom is dimethylaminoethyl acrylate, which is quaternized with an alkyl halide, or with methyl chloride or benzyl chloride or dimethyl sulfate (ADAME-Quat). In an embodiment, the cationic monomer when based on (meth)acrylamides are quaternized dialkylaminoalkyl(meth)acrylamides with C1 to C3 in the alkyl and alkylene groups, or dimethylaminopropylacrylamide, which is quaternized with an alkyl halide, or methyl chloride or benzyl chloride or dimethyl sulfate.

In an embodiment, the cationic monomer based on a (meth)acrylamide is a quaternized dialkylaminoalkyl(meth)acrylamide with C1 to C3 in the alkyl and alkylene groups. In an embodiment, the cationic monomer based on a (meth)acrylamide is dimethylaminopropylacrylamide, which is quaternized with an alkyl halide, especially methyl chloride or benzyl chloride or dimethyl sulfate.

In an embodiment, the cationic monomer is a hydrolysis-stable cationic monomer. Hydrolysis-stable cationic monomers can be, in addition to a dialkylaminoalkyl(meth)acrylamide, all monomers that can be regarded as stable to the OECD hydrolysis test. In an embodiment, the cationic monomer is hydrolysis-stable and the hydrolysis-stable cationic monomer is selected from the group consisting of: diallyldimethylammonium chloride and water-soluble, cationic styrene derivatives.

In an embodiment, the cationic copolymer is a terpolymer of acrylamide, 2-dimethylammoniumethyl (meth)acrylate quaternized with methyl chloride (ADAME-Q) and 3-dimethylammoniumpropyl(meth)acrylamide quaternized with methyl chloride (DIMAPA-Q). In an embodiment, the cationic copolymer is formed from acrylamide and acrylamidopropyltrimethylammonium chloride, wherein the acrylamidopropyltrimethylammonium chloride has a charge density of from about 1.0 meq/g to about 3.0 meq/g.

In an embodiment, the cationic copolymer has a charge density of from about 1.1 meq/g to about 2.5 meq/g, or from about 1.1 meq/g to about 2.3 meq/g, or from about 1.2 meq/g to about 2.2 meq/g, or from about 1.2 meq/g to about 2.1 meq/g, or from about 1.3 meq/g to about 2.0 meq/g, or from about 1.3 meq/g to about 1.9 meq/g.

In an embodiment, the cationic copolymer has a M.Wt. from about 100 thousand g/mol to about 2 million g/mol, or from about 300 thousand g/mol to about 1.8 million g/mol, or from about 500 thousand g/mol to about 1.6 million g/mol, or from about 700 thousand g/mol to about 1.4 million g/mol, or from about 900 thousand g/mol to about 1.2 million g/mol.

In an embodiment, the cationic copolymer is a trimethylammoniopropylmethacrylamide chloride-N-Acrylamide copolymer, which is also known as AM:MAPTAC. AM:MAPTAC may have a charge density of about 1.3 meq/g and a M.Wt. of about 1.1 million g/mol. In an embodiment, the cationic copolymer is AM:ATPAC. AM:ATPAC may have a charge density of about 1.8 meq/g and a M.Wt. of about 1.1 million g/mol.

In an embodiment, the cationic guar polymer (a) and the cationic copolymer (b) are used in the composition/added to the composition as a blend. Such a blend is disclosed in US2011/0002868A1 (Bierganns et al, filed Jul. 1, 2010), which is incorporated herein by reference. In particular, referring to the published text of US2011/0002868A1, paragraphs 0042 to 0047 describe cationic copolymers and paragraphs 0092 to 0095 describe inter alia cationic guar polymers. In an embodiment, the blend comprises the cationic guar polymer (a) and the cationic copolymer (b), wherein the cationic copolymer is AM:APTAC. For example, blends of cationic guar and AM:APTAC that are within the scope of this invention are available from Ashland. For example, a blend from Ashland is available, which is a blend of 95:5 guar hydroxypropyltrimonium chloride (M.Wt. 500,000 g/mol; charge density 1.1 meq/g) to AM/APTAC (M.Wt. 1.1 million g/mol; charge density 1.8 meq/g) i.e. a ratio of 19:1 cationic guar polymer (a) to the cationic copolymer (b).

The blend may comprise a cationic copolymer, wherein the cationic copolymer is formed from (1) copolymers of (meth)acrylamide and cationic monomers based on (meth)acrylamide, and/or hydrolysis-stable cationic monomers, (2)

terpolymers of (meth)acrylamide, monomers based on cationic (meth)acrylic acid esters, and monomers based on (meth)acrylamide, and/or hydrolysis-stable cationic monomers. In an embodiment, the blend is a combination of a cationic, water-soluble, synthetic copolymer and a polygalactomannan or a polyglucomannan, wherein the polygalactomannan and the polyglucomannan are derived from guar and contain quaternary ammonium groups covalently attached to the polysaccharide backbone. In an embodiment, said polygalactomannan or said polyglucomannan have a cationic degree of substitution (DS) is from about 0.03 to about 0.70. In an embodiment, said polygalactomannan or said polyglucomannan have a charge density of from about 0.1 to about 2.5 meq/g.

The sum of (a)+(b) is an amount of from about 0.0001% to about 0.7%, by total weight of the composition. The sum of (a)+(b) means the total weight percentage of cationic guar polymer as defined herein and cationic copolymer as defined herein, by total weight of the composition. In an embodiment, the sum of (a)+(b) is from about 0.01% to about 0.7%, or from about 0.1% to about 0.5%, or from about 0.1% to about 0.4%, or from about 0.2% to about 0.3%, by total weight of the composition. The sum of (a)+(b) is at the amount defined herein because above this level, the coacervate floc size starts to become too large for achieving good benefit. Larger floc size results in more coacervate particles being trapped between hair fibres and therefore do not effectively reach the scalp i.e. lower on-scalp deposition and hence cannot so effectively deliver the benefit. In a further embodiment, the sum of (a)+(b) is from about 0.0001% to less than about 0.6%, by total weight of the composition, from about 0.01% to less than about 0.6%, or from about 0.1% to less than about 0.5%, or from about 0.1% to less than about 0.4%, or from about 0.2% to less than about 0.3%, by total weight of the composition.

The weight ratio of (a):(b) is from about 1000:1 to about 2:1. In an embodiment, the weight ratio of (a):(b) is from about 1000:1 to about 4:1. In an embodiment, weight ratio of (a):(b) is from about 800:1 to about 4:1, or from about 500:1 to about 4:1, or from about 100:1 to about 5:1, or from about 100:1 to about 6:1, or from about 50:1 to about 6.5:1, or from about 50:1 to about 7:1, or from about 50:1 to about 8.3:1, or from about 50:1 to about 16.7:1.

The pH of the composition may be from about pH 3 to about pH 9, or from about pH 4 to about pH 7.

The composition comprises an anti-dandruff active, which may be an anti-dandruff active particulate. In an embodiment, the anti-dandruff active is selected from the group consisting of: pyridinethione salts; zinc carbonate; azoles, such as ketoconazole, econazole, and elubiol; selenium sulphide; particulate sulfur; keratolytic agents such as salicylic acid; and mixtures thereof. In an embodiment, the anti-dandruff particulate is a pyridinethione salt. Such anti-dandruff particulate should be physically and chemically compatible with the components of the composition, and should not otherwise unduly impair product stability, aesthetics or performance Pyridinethione particulates are suitable particulate anti-dandruff actives for use in composition of the present invention. In an embodiment, the anti-dandruff active is a 1-hydroxy-2-pyridinethione salt and is in particulate form. In an embodiment, the concentration of pyridinethione anti-dandruff particulate ranges from about 0.01% to about 5%, by weight of the composition, or from about 0.1% to about 3%, or from about 0.1% to about 2%. In an embodiment, the pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"), commonly 1-hydroxy-2-pyridinethione salts in platelet particle form. In an embodiment, the 1-hydroxy-2-pyridinethione salts in platelet particle form have an average particle size of up to about 20 microns, or up to about 5 microns, or up to about 2.5 microns. Salts formed from other cations, such as sodium, may also be suitable. Pyridinethione anti-dandruff actives are described, for example, in U.S. Pat. No. 2,809,971; 3,236,733; 3,753,196; 3,761,418; 4,345,080; 4,323,683; 4,379,753; and 4,470,982.

In an embodiment, in addition to the anti-dandruff active selected from polyvalent metal salts of pyrithione, the composition further comprises one or more anti-fungal and/or anti-microbial actives. In an embodiment, the anti-microbial active is selected from the group consisting of: coal tar, sulfur, fcharcoal, whitfield's ointment, castellani's paint, aluminum chloride, gentian violet, octopirox (piroctone olamine), ciclopirox olamine, undecylenic acid and its metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof. In an embodiment, the anti-microbial is selected from the group consisting of: itraconazole, ketoconazole, selenium sulphide, coal tar, and mixtures thereof.

In an embodiment, the azole anti-microbials is an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. When present in the composition, the azole anti-microbial active is included in an amount of from about 0.01% to about 5%, or from about 0.1% to about 3%, or from about 0.3% to about 2%, by total weight of the composition. In an embodiment, the azole anti-microbial active is ketoconazole. In an embodiment, the sole anti-microbial active is ketoconazole.

The present invention may also comprise a combination of anti-microbial actives. In an embodiment, the combination of anti-microbial active is selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbasole, octopirox and climbasole, salicylic acid and octopirox, and mixtures thereof.

In an embodiment, the composition comprises an effective amount of a zinc-containing layered material. In an embodiment, the composition comprises from about 0.001% to about 10%, or from about 0.01% to about 7%, or from about 0.1% to about 5% of a zinc-containing layered material, by total weight of the composition.

Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. In an embodiment, the ZLM is selected from the group consisting of: hydrozincite (zinc carbonate hydroxide), basic zinc carbonate, aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. In an embodiment, the ZLM is a layered double hydroxide conforming to the formula $[M^{2+}_{1-x}M^{3+}_x(OH)_2]^{x+}A^{m-}_{x/m} \cdot nH_2O$ wherein some or all of the divalent ions ($M^{2+}$) are zinc ions (Crepaldi, E L, Pava, P C, Tronto, J, Valim, J B *J. Colloid Interfac. Sci.* 2002, 248, 429-42).

Yet another class of ZLMs can be prepared called hydroxy double salts (Morioka, H., Tagaya, H., Karasu, M, Kadokawa, J, Chiba, K *Inorg. Chem.* 1999, 38, 4211-6). In an embodiment, the ZLM is a hydroxy double salt conforming to the formula $[M^{2+}_{1-x}M^{2+}_{1+x}(OH)_{3(1-y)}]^+ A^{n-}_{(1=3y)/n} \cdot nH_2O$ where the two metal ions ($M^{2+}$) may be the same or different. If they are the same and represented by zinc, the formula simplifies to $[Zn_{1+x}(OH)_2]^{2x+}2xA^- \cdot nH_2O$. This latter formula represents (where x=0.4) materials such as zinc hydroxychloride and zinc hydroxynitrate. In an embodiment, the ZLM is zinc hydroxychloride and/or zinc hydroxynitrate. These are related to hydrozincite as well wherein a divalent anion replace the monovalent anion. These materials can also be formed in situ in a composition or in or during a production process.

In an embodiment, the composition comprises basic zinc carbonate. Commercially available sources of basic zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union Corp.: New York, N.Y., USA), Zinc Carbonate (Elementis Pigments: Durham, UK), and Zinc Carbonate AC (Bruggemann Chemical: Newtown Square, Pa., USA). Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

In embodiments having a zinc-containing layered material and a pyrithione or polyvalent metal salt of pyrithione, the ratio of zinc-containing layered material to pyrithione or a polyvalent metal salt of pyrithione is from about 5:100 to about 10:1, or from about 2:10 to about 5:1, or from about 1:2 to about 3:1.

The on-scalp deposition of the anti-dandruff active is at least about 1 microgram/cm². The on-scalp deposition of the anti-dandruff active is important in view of ensuring that the anti-dandruff active reaches the scalp where it is able to perform its function. In an embodiment, the deposition of the anti-dandruff active on the scalp is at least about 1.5 microgram/cm², or at least about 2.5 microgram/cm², or at least about 3 microgram/cm², or at least about 4 microgram/cm², or at least about 6 microgram/cm², or at least about 7 microgram/cm², or at least about 8 microgram/cm², or at least about 8 microgram/cm², or at least about 10 microgram/cm². The on-scalp deposition of the anti-dandruff active is measured by having the hair of individuals washed with a composition comprising an anti-dandruff active, for example a composition pursuant to the present invention, by trained a cosmetician according to a conventional washing protocol. The hair is then parted on an area of the scalp to allow an open-ended glass cylinder to be held on the surface while an aliquot of an extraction solution is added and agitated prior to recovery and analytical determination of anti-dandruff active content by conventional methodology, such as HPLC.

In an embodiment, the on-scalp deposition of basic zinc carbonate is at least about 1 microgram/cm².

The composition comprises a cosmetically acceptable carrier. In an embodiment, the carrier is an aqueous carrier. The amount and chemistry of the carrier is selected according to the compatibility with other components and other desired characteristic of the product. In an embodiment, the carrier is selected from the group consisting of: water and water solutions of lower alkyl alcohols. In an embodiment, the carrier is a lower alkyl alcohol, wherein the monohydric alcohol has 1 to 6 carbons. In an embodiment, the carrier is ethanol and/or isopropanol. In an embodiment, the cosmetically acceptable carrier is a cosmetically acceptable aqueous carrier and is present at a level of from about 20% to about 95%, or from about 60% to about 85%.

The composition comprises a surfactant. The surfactant is included to provide cleaning performance to the composition. In an embodiment, the surfactant is selected from the group consisting of: anionic surfactants, amphoteric surfactants, zwitterionic surfactants, cationic surfactants, nonionic surfactants, and mixtures thereof. In an embodiment, the surfactant is an anionic surfactant. In an embodiment, the composition comprises from about 5% to about 50%, or from about 8% to about 30%, or from about 10% to about 25% of a surfactant, by total weight of the composition.

The composition may comprise a detersive surfactant system. The detersive surfactant system may comprise at least one anionic surfactant, and optionally a co-surfactant selected from the group consisting of: an amphoteric surfactant, a zwitterionic surfactant, a cationic surfactant, a nonionic surfactant, or a mixture thereof. The concentration of the detersive surfactant system in the composition should be sufficient to provide the desired cleaning and lather performance. In an embodiment, the composition comprises from about 5% to about 50%, or from about 8% to about 30%, or from about 10% to about 25% of detersive surfactant system, by total weight of the composition.

In considering the performance characteristics, such as coacervate formation, wet conditioning performance, dry conditioning performance, and conditioning agent deposition on hair, it is desirable to optimize the levels and types of surfactants in order to maximize the performance potential of polymer systems. In one embodiment, the detersive surfactant system for use in the composition comprises an anionic surfactant with an ethoxylate level and an anion level, wherein the ethoxylate level is from about 1 to about 10, and wherein the anion level is from about 1 to about 10.

The combination of such an anionic surfactant with the cationic copolymer and cationic guar polymer provides enhanced deposition of conditioning agents to hair and/or skin without reducing cleansing or lathering performance. An optimal ethoxylate level is calculated based on the stoichiometry of the surfactant structure, which in turn is based on a particular M.Wt. of the surfactant where the number of moles of ethoxylation is known. Likewise, given a specific M.Wt. of a surfactant and an anionization reaction completion measurement, the anion level can be calculated.

In an embodiment, the detersive surfactant system comprises at least one anionic surfactant comprising an anion selected from the group consisting of sulfates, sulfonates, sulfosuccinates, isethionates, carboxylates, phosphates, and phosphonates. In an embodiment, the anion is a sulfate.

In an embodiment, the anionic surfactant is an alkyl sulfate or an alkyl ether sulfate. These materials have the respective formulae $R^9OSO_3M$ and $R^9O(C_2H_4O)_xSO_3M$, wherein $R^9$ is alkyl or alkenyl of from about 8 to about 18 carbon atoms, x is an integer having a value of from about 1 to about 10, and M is a cation such as ammonium, an alkanolamine such as triethanolamine, a monovalent metal cation such as sodium and potassium, or a polyvalent metal cation such as magnesium and calcium. Solubility of the surfactant will depend upon the particular anionic surfactants and cations chosen. In an embodiment, $R^9$ has from about 8 to about 18 carbon atoms, or from about 10 to about 16 carbon atoms, or from about 12 to about 14 carbon atoms, in both the alkyl sulfates and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. In an embodiment, the alcohols are lauryl alcohol and straight chain alcohols derived from coconut oil or palm kernel oil. Such alcohols are reacted with from about 0 to about 10, or from about 2 to about 5, or about 3, molar proportions of ethylene oxide, and the resulting mixture of molecular species having, for example, an average of 3 moles of ethylene oxide per mole of alcohol is sulfated and neutralized. In an embodiment, the alkyl ether sulphate is selected from the group consisting of: sodium and ammonium salts of coconut alkyl triethylene glycol ether sulfate, tallow alkyl triethylene glycol ether sulfate, tallow alkyl hexa-oxyethylene sulphate, and mixtures thereof. In an embodiment, the alkyl ether sulfate comprises a mixture of individual compounds, wherein the compounds in the mixture have an average alkyl chain length of from about 10 to about 16 carbon atoms and an average degree of ethoxylation of from about 1 to about 4 moles of ethylene oxide. Such a mixture also comprises from about 0% to about 20% $C_{12-13}$ compounds; from about 60% to about 100% of $C_{14-15-16}$ compounds; from about 0% to about 20% by weight of $C_{17-18-19}$ compounds; from about 3% to about 30% by weight of compounds having a degree of ethoxylation of 0; from about 45% to about 90% by weight of compounds having a degree of ethoxylation from about 1 to about 4; from about 10% to about 25% by weight of compounds having a degree of ethoxylation from about 4 to about 8; and from about 0.1% to about 15% by weight of compounds having a degree of ethoxylation greater than about 8.

In an embodiment, the anionic surfactant is selected from the group consisting of: ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, and mixtures thereof. In addition to the sulfates, isethionates, sulfonates, sulfosuccinates described above, other potential anions for the anionic surfactant include phosphonates, phosphates, and carboxylates.

The composition and/or the detersive surfactant system may comprise a co-surfactant selected from the group consisting of: amphoteric surfactants, zwitterionic surfactants, cationic surfactants, non-ionic surfactants, and mixtures thereof. The concentration of such co-surfactants may be from about 0.5% to about 20%, or from about 1% to about 10%, by total weight of the composition. In an embodiment, the composition comprises a co-surfactant selected from the group consisting of: amphoteric surfactants, zwitterionic surfactants, and mixtures thereof. Non limiting examples of suitable zwitterionic or amphoteric surfactants are described in U.S. Pat. No. 5,104,646 (Bolich Jr. et al.), U.S. Pat. No. 5,106,609 (Bolich Jr. et al.).

Amphoteric surfactants suitable for use in the composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. In an embodiment, the amphoteric surfactant is selected from the group consisting of: sodium cocaminopropionate, sodium cocaminodipropionate, sodium cocoamphoacetate, sodium cocoamphohydroxypropylsulfonate, sodium cocoamphopropionate, sodium cornamphopropionate, sodium lauraminopropionate, sodium lauroamphoacetate, sodium lauroamphohydroxypropylsulfonate, sodium lauroamphopropionate, sodium cornamphopropionate, sodium lauriminodipropionate, ammonium cocaminopropionate, ammonium cocaminodipropionate, ammonium cocoamphoacetate, ammonium cocoamphohydroxypropylsulfonate, ammonium cocoamphopropionate, ammonium cornamphopropionate, ammonium lauraminopropionate, ammonium lauroamphoacetate, ammonium lauroamphohydroxypropylsulfonate, ammonium lauroamphopropionate, ammonium cornamphopropionate, ammonium lauriminodipropionate, triethanonlamine cocaminopropionate, triethanonlamine cocaminodipropionate, triethanonlamine cocoamphoacetate, triethanonlamine cocoamphohydroxypropylsulfonate, triethanonlamine cocoamphopropionate, triethanonlamine cornamphopropionate, triethanonlamine lauraminopropionate, triethanonlamine lauroamphoacetate, triethanonlamine lauroamphohydroxypropylsulfonate, triethanonlamine lauroamphopropionate, triethanonlamine cornamphopropionate, triethanonlamine lauriminodipropionate, cocoamphodipropionic acid, disodium caproamphodiacetate, disodium caproamphoadipropionate, disodium capryloamphodiacetate, disodium capryloamphodipriopionate, disodium cocoamphocarboxyethylhydroxypropylsulfonate, disodium cocoamphodiacetate, disodium cocoamphodipropionate, disodium dicarboxyethylcocopropylenediamine, disodium laureth-5 carboxyamphodiacetate, disodium lauriminodipropionate, disodium lauroamphodiacetate, disodium lauroamphodipropionate, disodium oleoamphodipropionate, disodium PPG-2-isodecethy-7 carboxyamphodiacetate, lauraminopropionic acid, lauroamphodipropionic acid, lauryl aminopropylglycine, lauryl diethylenediaminoglycine, and mixtures thereof.

In one embodiment, the amphoteric surfactant is a surfactant according to the following structure:

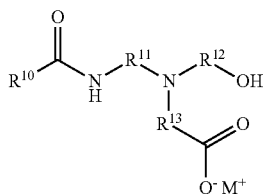

wherein $R^{10}$ is a C-linked monovalent substituent selected from the group consisting of: substituted alkyl systems comprising 9 to 15 carbon atoms, unsubstituted alkyl systems comprising 9 to 15 carbon atoms, straight alkyl systems comprising 9 to 15 carbon atoms, branched alkyl systems comprising 9 to 15 carbon atoms, and unsaturated alkyl systems comprising 9 to 15 carbon atoms; and wherein $R^{11}$, $R^{12}$, and $R^{13}$ are each independently selected from the group consisting of: C-linked divalent straight alkyl systems comprising 1 to 3 carbon atoms, and C-linked divalent branched alkyl systems comprising 1 to 3 carbon atoms; and wherein $M^+$ is a monovalent counterion selected from the group consisting of sodium, ammonium and protonated triethanolamine. In an embodiment, the amphoteric surfactant is selected from the group consisting of: sodium cocoamphoacetate, sodium cocoamphodiacetate, sodium lauroamphoacetate, sodium lauroamphodiacetate, ammonium lauroamphoacetate, ammonium cocoamphoacetate, triethanolamine lauroamphoacetate, triethanolamine cocoamphoacetate, and mixtures thereof.

In an embodiment, the composition comprises a zwitterionic surfactant, wherein the zwitterionic surfactant is a derivative of an aliphatic quaternary ammonium, phosphonium, and sulfonium compound, in which the aliphatic radicals are straight or branched chain, and wherein one of the aliphatic substituents contains from about 8 to about 18 carbon atoms and one contains an anionic group such as carboxy, sulfonate, sulfate, phosphate or phosphonate. In an embodiment, the zwitterionic surfactant is selected from the group consisting of: cocamidoethyl betaine, cocamidopropylamine oxide, cocamidopropyl betaine, cocamidopropyl dimethylaminohydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coco/oleamidopropyl betaine, coco-sultaine, lauramidopropyl betaine, lauryl betaine, lauryl hydroxysultaine, lauryl sultaine, and mixtures thereof. In an embodiment, the zwitterionic surfactant is selected from the group consisting of: lauryl hydroxysultaine, cocamidopropyl hydroxysultaine, coco-betaine, coco-hydroxysultaine, coco-sultaine, lauryl betaine, lauryl sultaine, and mixtures thereof.

In an embodiment, the co-surfactant is selected from the group consisting of: zwitterionic surfactants, amphoteric surfactants, non-ionic surfactants, and mixtures thereof. In an embodiment, the surfactant is an anionic surfactant and the composition further comprises a co-surfactant, wherein the co-surfactant is selected from the group consisting of: zwitterionic surfactants, amphoteric surfactants, non-ionic surfactants, and mixtures thereof. In an embodiment, the co-surfactant is a non-ionic surfactant selected from the group consisting of: Cocamide, Cocamide Methyl MEA, Cocamide DEA, Cocamide MEA, Cocamide MIPA, Lauramide DEA, Lauramide MEA, Lauramide MIPA, Myristamide DEA, Myristamide MEA, PEG-20 Cocamide MEA, PEG-2 Cocamide, PEG-3 Cocamide, PEG-4 Cocamide, PEG-5 Cocamide, PEG-6 Cocamide, PEG-7 Cocamide, PEG-3 Lauramide, PEG-5 Lauramide, PEG-3 Oleamide, PPG-2 Cocamide, PPG-2 Hydroxyethyl Cocamide, and mixtures thereof. In an embodiment, the co-surfactant is a zwitterionic surfactant, wherein the zwitterionic surfactant is selected from the group consisting of: lauryl hydroxysultaine, cocamidopropyl hydroxysultaine, coco-betaine, cocohydroxysultaine, coco-sultaine, lauryl betaine, lauryl sultaine, and mixtures thereof.

In accordance with an embodiment of the present invention, the composition further includes an insoluble polysiloxane. It has been surprisingly found that, by formulating personal care composition with a silicone emulsion of an insoluble polysiloxane, e.g., poly-dimethylsiloxane, having at total content of cyclic polysiloxane of less than 2.5 wt % based on the total weight of all polysiloxanes, in combination with cationic guar polymers and/or cationic copolymers of acrylamide monomers and cationic monomers, improves the deposition of the conditioning polymer and the insoluble polysiloxane on the skin and hair can be improved with minimal or no consumer unacceptance of hair conditioning and hair feel.

Without being bound by any particular theory, it is believed that insoluble polysiloxanes emulsions having levels of cyclic polysiloxanes below the aforementioned threshold, provide improved consumer acceptance of hair conditioning and hair feel and yet also excellent on-scalp deposition. It is believed that cyclic polysiloxanes disrupt higher order surfactant micelle formation, which in turn requires increasing the amount of salt to be added to the composition in order to achieve acceptable rheology parameters of the composition. However, the observed increase in viscosity induced by the increased salt content may also be associated with an increased floc size of the coacervate. Increasing floc size can negatively affect the on-scalp deposition, for example, by a larger floc becoming trapped in the hair. By blending an anionic surfactant, a cationic conditioning polymer, and the silicone emulsion defined herein, it has been surprisingly found that both the consumer desirable benefits of the lower molecular weight cationic guars and the enhanced deposition of the cationic copolymers and silicone can be achieved in a single composition while still preserving the consumer desirability. Advantageously, this combination of surfactant, polymer and silicone is useful for the deposition of actives, such as anti-dandruff actives.

More specifically, it is believed that an insoluble polysiloxane of a desired particle size (<10 micron) in the embodiments of the present invention can be delivered to the hair and scalp via entrapment in the coacervate microstructure. Insoluble polysiloxane species entrapped in the coacervate microstructure result in a less tightly bound structure which can be characteristic of high deposition systems like cationic guar/synthetic co-polymer systems. Less tightly bound coacervate microstructures can be characterized by reduced complex coacervate rheology (CCR).

The impact of the silicone emulsion further dictates the achievement of the desired reduction of coacervate floc size and rheology. In general, silicone microemulsions and nanoemulsions contain various amounts of residual cyclic polysiloxanes. For example, dimethiconol may include significant quantities of cyclic polysiloxanes, such as octamethylcyclotetrasiloxane and decamethylcyclotetrasiloxane. The cyclic polysiloxanes can significantly impact anionic surfactant based compositions, such as shampoos, by disrupting higher order surfactant micelle formation, which is critical for achieving consumer accepted compositional viscosity targets. As a consequence of the higher order micelle formation disruption, higher levels of NaCl are added to the personal care composition in order to compensate for the drop in viscosity. However, increasing the salt level produces a larger coacervate particle size, which has been shown to result in a negative cosmetic experience. Accordingly, silicone emulsions of polysiloxanes with cyclic polysiloxanes below specified levels unexpectedly yield excellent deposition and quality, while providing improved hair feel.

The features of the composition according to the first aspect, as well as the other aspects and other relevant components, are described in detail hereinafter. All components of the composition described herein should be physically and chemically compatible with the essential components described herein, and should not otherwise unduly impair product stability, aesthetics or performance.

In accordance with one embodiment of the present invention, a personal care composition is provided, comprising: a) an anionic surfactant; b) a cationic conditioning polymer; and c) a silicone emulsion comprising an insoluble polysiloxane.

A. Silicone Emulsion

The silicone emulsions suitable for use in the embodiments of the present invention include emulsions of insoluble polysiloxanes prepared in accordance with the descriptions provided in U.S. Pat. No. 4,476,282 and U.S. Patent Application Publication No. 2007/0276087. Accordingly, insoluble polysiloxanes referred to herein for the purpose of the invention include polysiloxanes such as alpha, omega hydroxy-terminated polysiloxanes or alpha, omega alkoxy-terminated polysiloxanes having a molecular weight within the range from about 50,000 to about 500,000 g/mol. As used herein, "insoluble polysiloxane" means that the water solubility of the polysiloxane is less than 0.05 wt %. In another embodiment, the water solubility of the polysiloxane is less than 0.02 wt %, or less than 0.01 wt %, or less than 0.001 wt %. According to an embodiment, the insoluble polysiloxane is present in the personal care composition in an amount within the range from about 0.1 wt % to about 3 wt %, based on the total weight of the composition. For example, the insoluble polysiloxane can be present in an amount within the range from about 0.2 wt % to about 2.5 wt %, or from about 0.4 wt % to about 2.0 wt %, or from about 0.5 wt % to about 1.5 wt %, based on the total weight of the composition.

According to one aspect of the silicone emulsion, the insoluble polysiloxane used herein include alpha, omega hydroxy- or alkoxy-terminated polysiloxanes having a general formula I:

$$R^{15}—[O—Si(R^{14})_2]_n—OR^{15},$$

wherein 'n' is an integer, $R^{14}$ is a substituted or unsubstituted $C_1$ to $C_{10}$ alkyl or aryl, and $R^{15}$ is a hydrogen or a substituted or unsubstituted $C_1$ to $C_{10}$ alkyl or aryl. Non-limiting examples of $R^{14}$ and $R^{15}$ may be independently selected from alkyl groups such as methyl, ethyl, n-propyl, isopropyl, n-butyl, isobutyl, tert-butyl, n-pentyl, isopentyl, neopentyl, tertpentyl, hexyl such as n-hexyl, heptyl such as n-heptyl, octyl such as n-octyl and isooctyl such as 2,2,4-trimethyl-pentyl, nonyl such as n-nonyl, decyl such as n-decyl, dodecyl such as n-dodecyl, octadecyl such as n-octadecyl; or aryl groups such as phenyl, naphthyl, anthryl and phenanthryl. In an embodiment, the insoluble polysiloxane has a general formula H—[O—Si($R^{14}$)$_2$]$_n$—OH.

According to another aspect of the silicone emulsion, the insoluble polysiloxane has an average molecular weight within the range from about 50,000 to about 500,000 g/mol. For example, the insoluble polysiloxane may have an average molecular weight within the range from about 60,000 to about 400,000; from about 75,000 to about 300,000; from about 100,000 to about 200,000; or the average molecular weight may be about 150,000 g/mol.

According to another aspect of the silicon emulsion, total content of a cyclic polysiloxane having a general formula:

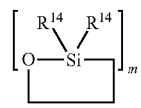

wherein $R^{14}$ is as defined above, and wherein m is 4 or 5, is present in the silicone emulsion in an amount less than about 2.5 wt % based on the total weight of all polysiloxanes. For example, dimethiconol may include significant quantities of cyclic polysiloxanes, such as octamethylcyclotetrasiloxane (D4) and decamethylcyclotetrasiloxane (D5). In an embodiment, the amount of D4 is less than about 2.0%, or less than about 1.5%, or less than about 1.0%, or less than about 0.5%, based on the total weight of all polysiloxanes. In an embodiment, the amount of D5 is less than about 0.5%, or less than about 0.4%, or less than about 0.3%, or less than about 0.2%, based on the total weight of all polysiloxanes.

According to yet another aspect of the silicone emulsion, the emulsion has a viscosity up to about 500,000 cPs. For example, the viscosity may be within the range from about 75,000 to about 300,000, from about 100,000 to about 200,000, or about 150,000 cPs.

According to yet another aspect of the silicone emulsion, the insoluble polysiloxane has an average particle size within the range from about 30 nm to about 10 micron. The average particle size may be within the range from about 40 nm to about 5 micron, from about 50 nm to about 1 micron, from about 75 nm to about 500 nm, or about 100 nm, for example.

The average molecular weight of the insoluble polysiloxane, the viscosity of the silicone emulsion, and the size of the particle comprising the insoluble polysiloxane are determined by methods commonly used by those skilled in the art, such as the methods disclosed in Smith, A. L. *The Analytical Chemistry of Silicones*, John Wiley & Sons, Inc.: New York, 1991.

According to another aspect of the silicone emulsion, the emulsion further includes an anionic surfactant that participates in providing high internal phase viscosity emulsions having particle sizes in the range from about 30 nm to about 10 micron. The anionic surfactant is selected from organic sulfonic acids. Most common sulfonic acids used in the present process are alkylaryl sulfonic acid; alkylaryl polyoxyethylene sulphonic acid; alkyl sulfonic acid; and alkyl polyoxyethylene sulfonic acid. General formulas of the sulfonic acids are as shown below:

$$R^{16}C_6H_4SO_3H \quad \text{(II)}$$

$$R^{16}C_6H_4O(C_2H_4O)_mSO_3H \quad \text{(III)}$$

$$R^{16}SO_3H \quad \text{(IV)}$$

$$R^{16}O(C_2H_4O)_mSO_3H \quad \text{(IV)}$$

Where $R^{16}$, which may differ, is a monovalent hydrocarbon radical having at least 6 carbon atoms. Non-limiting examples of $R^{16}$ include hexyl, octyl, decyl, dodecyl, cetyl, stearyl, myristyl, and oleyl. 'm' is an integer from 1 to 25. Exemplary anionic surfactants include but are not limited to octylbenzene sulfonic acid; dodecylbenzene sulfonic acid; cetylbenzene sulfonic acid; alpha-octyl sulfonic acid; alpha-dodecyl sulfonic acid; alpha-cetyl sulfonic acid; polyoxyethylene octylbenzene sulfonic acid; polyoxyethylene dodecylbenzene sulfonic acid; polyoxyethylene cetylbenzene sulfonic acid; polyoxyethylene octyl sulfonic acid; polyoxyethylene dodecyl sulfonic acid; and polyoxyethylene cetyl sulfonic acid. Generally, 1 to 15% anionic surfactant is used in the emulsion process. For example, 3-10% anionic surfactant can be used to obtain an optimum result.

The silicone emulsion may further include an additional emulsifier together with the anionic surfactant, which along with the controlled temperature of emulsification and polymerization, facilitates making the emulsion in a simple and faster way. Non-ionic emulsifiers having a hydrophilic lipophilic balance (HLB) value of 10 to 19 are suitable and include polyoxyalkylene alkyl ether, polyoxyalkylene alkylphenyl ethers and polyoxyalkylene sorbitan esters. Some useful emulsifiers having an HLB value of 10 to 19 include, but are not limited to, polyethylene glycol octyl ether; polyethylene glycol lauryl ether; polyethylene glycol tridecyl ether; polyethylene glycol cetyl ether; polyethylene glycol stearyl ether; polyethylene glycol nonylphenyl ether; polyethylene glycol dodecylphenyl ether; polyethylene glycol cetylphenyl ether; polyethylene glycol stearylphenyl ether; polyethylene glycol sorbitan mono stearate; and polyethylene glycol sorbitan mono oleate.

In accordance with embodiments of the present invention, the personal care composition may further comprise one or more benefit agents. Exemplary benefit agents include, but are not limited to, particles, colorants, perfume microcapsules, gel networks, and other insoluble skin or hair conditioning agents such as skin silicones, natural oils such as sun flower oil or castor oil. In an embodiment, the benefit agent is selected from the group consisting of: particles; colorants; perfume microcapsules; gel networks; other insoluble skin or hair conditioning agents such as skin silicones, natural oils such as sun flower oil or castor oil; and mixtures thereof.

The composition forms coacervate particles upon dilution of the composition with water. The percentage of coacervate particles with a floc size of greater than about 20 micron is from about 1% to about 60%. In an embodiment, the percentage of coacervate particles with a floc size of greater than about 20 micron is from about 1% to about 50%, or from about 1% to about 40%, or from about 1% to about 30%, or from about 5% to about 20% from about 5% to about 15%. The floc size is measured after diluting the composition 1:50 dilution with water.

The floc size may be measured using a Lasentec FBRM Method: In a suitable mixing vessel create a 1:9 dilution of composition in distilled water at ambient temperature and mix for 5 min at 250 rpm. Using a peristaltic pump transfer ambient distilled water into the mixing vessel at a rate of 100 g/min resulting in a final dilution of 1:50 parts composition to distilled water. After a 10 min equilibration period a Lasentec Focused Beam Reflectance Method (FBRM) [model S400A available from Mettler Toledo Corp] may be used to determine floc size and amount as measured by chord length and particle counts/sec (counts per sec).

The viscosity of the coacervate particles may be measured via squeeze flow resulting in a squeeze flow viscosity. The coacervate may be prepared and isolated for rheological testing as follows: A well-mixed 1:50 dilution of composition in distilled water is prepared at ambient temperature in such a quantity to produce a coacervate pellet of at least 3 grams after centrifugation at 4500 rpm for 30 min. The supernatant liquid is decanted and discarded and the coacervate pellet collected. A second centrifugation step is required for 15 min at 9100 rpm to ensure sample integrity prior to measurement. Any remaining supernatant liquid is removed without disturbing the coacervate pellet collected at the bottom of the container.

In the squeeze flow experiment, the coacervate to be tested is loaded between two parallel plates of radius R on a conventional rheometer (for example, 25 mm parallel plates on a TA AR2000) equilibrated to 25° C. Sufficient coacervate is added to completely fill a gap of 1000 microns, and any excess material is trimmed prior to starting the test. The sample is allowed to relax from loading stresses for 1 min. The top plate is lowered at a constant linear velocity as the gap is decreased. During this process the normal force exerted by the sample on the lower plate is measured by the rheometer. Typical linear velocities utilized for the squeeze experiment are 10 or 100 microns/sec. The gap is decreased from 1000 microns until a final gap of 100 microns is reached or until the normal force reaches the maximum instrument tolerance.

The measured force, F, and gap, h, are further analyzed to obtain a more traditional viscosity versus shear rate format. Analysis of squeezing flow between parallel plates for Newtonian and various non-Newtonian materials has been published in the literature (*J. of Non-Newtonian Fluid Mechanics*, 132 (2005) 1-27). A power-law model is chosen to describe the coacervate since it best describes the viscosity behavior in the nonlinear region. The power-law parameters K, the power-law consistency, and n, the power-law exponent, are determined from the corresponding expression for force as a function of gap under constant area, constant linear velocity, no-slip squeeze flow (*J. of Non-Newtonian Fluid Mechanics*, 132 (2005) 1-27). The nonlinear force versus gap expression is first linearized by taking the natural log of both sides of the expression. The power-law parameters K and n are then obtained from the slope and intercept of a fit to the linear region of ln(Force) versus ln(gap) and using the known constants from the experimental conditions. Utilizing these values of K and n, the squeeze flow viscosity i can be calculated at a specific shear rate $\dot{\gamma}$ via the power-law model:

$$\eta = K \cdot \dot{\gamma}^{(n-1)}$$

This relationship is used to determine the squeeze flow viscosity at a shear rate of 100 s$^{-1}$.

The composition forms coacervate particles upon dilution of the composition with water. The coacervate particles have a squeeze flow viscosity of from about 1 Pa·s to about 100 Pa·s, or from about 1 Pa·s to about 80 Pa·s, or from about 2 Pa·s to about 60 Pa·s, or from about 3 Pa·s to about 50 Pa·s, or from about 4 Pa·s to about 40 Pa·s, or from about 5 Pa·s to about 30 Pa·s, or from about 10 Pa·s to about 20 Pa·s, measured at 25° C. with a TA AR2000 rheometer at a 100 s$^{-1}$. Pa·s refers to Pascal seconds. These values relate to when the composition is diluted 1:50 with water (composition:water).

In an embodiment of the method, a mean consumer acceptance rating, on a scale of 1 to 100, of 60 or more, or 65 or more, or 70 or more, or 75 or more, or 80 or more, or 85 or more, is achieved. In order to obtain mean consumer acceptance rating values, compositions are evaluated by consumer panels ranging in size from 10 to 400, for example 16 to 310 people. Panelists are asked to use the composition as their only shampoo over a period of time ranging from 3 days to 4 weeks. After use, the panelists are asked to rate different attributes of the composition and its usage experience on a 5 point scale. For the purpose of numerical analysis, the answers are converted to a 100 point scale and the mean consumer acceptance rating calculated.

An alternative embodiment of the first aspect relates to a method for treating hair comprising applying to hair a composition comprising:
(a) a cationic guar polymer, wherein the cationic guar polymer has a weight average M.Wt. of less than about 1 million g/mol, and wherein the cationic guar polymer has a charge density of from about 0.1 meq/g to about 2.5 meq/g;
(b) a cationic copolymer of acrylamide monomers and cationic monomers, wherein the copolymer has a charge density of from about 1.0 meq/g to about 3.0 meq/g;
(c) an anti-dandruff active;
(d) a cosmetically acceptable carrier;
(e) a surfactant;
wherein the weight ratio of (a):(b) is from about 1000:1 to about 3.5:1;
and wherein the sum of (a)+(b) is an amount of from about 0.0001% to about 0.7%, by total weight of the composition.

In an embodiment of this alternative embodiment, the method further comprises diluting the composition with water, or diluting the composition 1:50 with water (composition:water). In an embodiment, after diluting the composition 1:50 with water, coacervate particles are formed, wherein the coacervate particles have a squeeze flow viscosity of from about 1 cP to about 100 cP, measured at 25° C. with a TA AR2000 rheometer at a 100 s$^{-1}$; and wherein the percentage of coacervate particles with a floc size of greater than about 20 micron is from about 1% to about 60%; and wherein the on-scalp deposition of the anti-dandruff active is at least about 1 microgram/cm$^2$. In an embodiment of this alternative embodiment, the method further comprises rinsing the hair.

According to the second aspect, the present invention relates to a hair conditioning composition comprising:
(a) a cationic guar polymer, wherein the cationic guar polymer has a weight average M.Wt. of less than about 1 million g/mol, and wherein the cationic guar polymer has a charge density of from about 0.1 meq/g to about 2.5 meq/g;
(b) a cationic copolymer of acrylamide monomers and cationic monomers, wherein the copolymer has a charge density of from about 1.0 meq/g to about 3.0 meq/g;
(c) an anti-dandruff active;
(d) a cosmetically acceptable carrier;
(e) a surfactant;
wherein the weight ratio of (a):(b) is from about 1000:1 to about 3.5:1;
and wherein the sum of (a)+(b) is an amount of from about 0.0001% to about 0.7%, by total weight of the composition.

The details of the composition described in relation to the first aspect also apply to the composition of the second aspect mutatis mutandis.

In an embodiment, the composition has a viscosity of 4,000 cP to 20,000 cP, or from about 6,000 cP to about 12,000 cP, or from about 8,000 cP to about 11,000 cP, measured at 26.6° C. with a Brookfield R/S Plus Rheometer at 2 s$^{-1}$. cP means centipoises.

In an embodiment, the composition is capable of forming coacervate particles upon 1:50 dilution of the composition with water; and wherein the coacervate particles have a squeeze flow viscosity of from about 1 cP to about 100 cP, measured at 25° C. with a TA AR2000 rheometer at a 100 s$^{-1}$; and wherein the percentage of coacervate particles with a floc size of greater than about 20 micron is from about 1% to about 60%; and wherein the on-scalp deposition of the anti-dandruff active is at least about 1 microgram/cm$^2$. The details of the coacervate and consumer acceptance described in relation to the first aspect also apply to the composition of the second aspect mutatis mutandis.

The third aspect relates to the use of the composition, according to the second aspect, for treating hair. In an embodiment, the use is for achieving improved hair feel and/or for reducing dandruff. The details of the composition described in relation to the first aspect also apply to the composition of the third aspect mutatis mutandis.

The fourth aspect relates to a kit comprising:
(a) application instructions comprising the method according to the first aspect; and
(b) a composition.

In an embodiment, the composition of the kit is the composition according to the second aspect. The details of the composition described in relation to the first aspect also apply to the composition of the fourth aspect mutatis mutandis. The details of the method described in relation to the first aspect also apply to the method of the fourth aspect mutatis mutandis.

EXAMPLES

The following examples illustrate the present invention. The exemplified compositions can be prepared by conventional formulation and mixing techniques. It will be appreciated that other modifications of the present invention within the skill of those in the hair care formulation art can be undertaken without departing from the spirit and scope of this invention. All parts, percentages, and ratios herein are by weight unless otherwise specified. Some components may come from suppliers as dilute solutions. The levels given reflect the weight percent of the active material, unless otherwise specified.

Examples 1 to 4, 8 and 9 are pursuant to the present invention and examples 5, 6, 7 and 10 to 11 are not.

|  | Example | | | | | | | | | | |
|---|---|---|---|---|---|---|---|---|---|---|---|
| Component | 1 | 2 | 3 | 4 | 5 | 6 | 7 | 8 | 9 | 10 | 11 |
| Guar hydroxypropyltrimonium chloride[1] | 0.3 | 0.3 | 0.27 | 0.27 | 0.27 | 0.27 | 0.3 | — | — | — | — |
| Guar hydroxypropyltrimonium chloride[2] | — | — | — | — | — | — | — | — | — | — | 0.1 |
| Guar hydroxypropyltrimonium chloride/ trimethylammoniopropyl-methacrylamide/acrylamide copolymer[3] | — | — | — | — | — | — | — | 0.25 | 0.4 | 0.6 | — |
| Acrylamide/Triquat[4] | 0.045 | 0.045 | 0.03 | 0.03 | 0.09 | 0.09 | 0.25 | — | — | — | 0.2 |
| Sodium laureth-3 sulfate[5] | — | — | 7.0 | 7.0 | 7.0 | 7.0 | 7.0 | — | — | — | — |
| Sodium laureth-1 sulfate[6] | 12.5 | 12.5 | — | — | — | — | — | 10.5 | 10.5 | 10.5 | 12.0 |
| Sodium Lauryl sulfate[7] | 1.5 | 1.5 | 7.0 | 7.0 | 7.0 | 7.0 | 7.0 | 1.5 | 1.5 | 1.5 | 1.5 |
| Cocamidopropyl betaine[8] | 1.5 | 1.5 | 1.5 | 1.5 | 1.5 | 1.5 | 1.5 | — | — | — | 1.0 |
| Coco betaine[9] | — | — | — | — | — | — | — | — | — | — | 1.5 |
| Cocamide MEA[10] | — | — | — | — | — | — | — | 1.0 | 1.0 | 1.0 | — |
| Lauryl hydroxysultaine[11] | — | — | — | — | — | — | — | 1.0 | 1.0 | 1.0 | — |
| Dimethicone[12] | — | — | 0.85 | 2.35 | 0.85 | 2.35 | 0.85 | — | — | — | — |
| Dimethiconol[13] | 1.0 | 1.0 | — | — | — | — | — | 1.0 | 1.0 | 1.0 | 1.0 |
| Zinc Pyrithione[14] | 1.0 | 1.0 | 1.0 | 1.0 | 1.0 | 1.0 | 1.0 | 1.0 | 1.0 | 1.0 | 1.0 |
| Zinc Carbonate[15] | 1.61 | 1.61 | 1.61 | 1.61 | 1.61 | 1.61 | 1.61 | 1.61 | 1.61 | 1.61 | 1.61 |
| Stearyl Alcohol[16] | — | 1.29 | — | — | — | — | — | — | — | — | — |
| Cetyl Alcohol[17] | — | 0.71 | — | — | — | — | — | — | — | — | — |
| Glycol distearate[18] | 1.5 | 1.5 | 1.5 | 1.5 | 1.5 | 1.5 | 1.5 | 1.5 | 1.5 | 1.5 | 1.5 |
| Preservative[19] | 0.05 | 0.05 | 0.05 | 0.05 | 0.05 | 0.05 | 0.05 | 0.05 | 0.05 | 0.05 | 0.05 |
| Sodium Benzoate | 0.25 | 0.25 | 0.25 | 0.25 | 0.25 | 0.25 | 0.25 | 0.25 | 0.25 | 0.25 | 0.25 |
| Fragrance | 0.75 | 0.75 | 0.75 | 0.75 | 0.75 | 0.75 | 0.75 | 0.75 | 0.75 | 0.75 | 0.75 |
| Hydrochloric Acid 6N | QS | QS | QS | QS | QS | QS | QS | QS | QS | QS | QS |
| Sodium Chloride | QS | QS | QS | QS | QS | QS | QS | QS | QS | QS | QS |
| Water | QS | QS | QS | QS | QS | QS | QS | QS | QS | QS | QS |
| Total | 100 | 100 | 100 | 100 | 100 | 100 | 100 | 100 | 100 | 100 | 100 |

KEY:
[1] Jaguar C500 from Rhodia with a M.Wt. of 500,000 g/mol and charge density of 0.8 meq/g.
[2] Jaguar Excel from Rhodia with a M.Wt. of 1,200,000 g/mol and charge density of 0.7 meq/g.
[3] A blend from Ashland, which is a blend of 95:5 guar hydroxypropyltrimonium chloride (M.Wt. 500,000 g/mol; charge density 1.1 meq/g) to AM/APTAC (M.Wt. 1.1 million g/mol; charge density 1.8 meq/g).
[4] Polyquaternium-76 (PQ-76) from Rhodia with a M.Wt. of 1,000,000 g/mol and charge density of 1.6 meq/g.
[5] Sodium laureth-3 sulfate from the Stepan Company
[6] Sodium laureth-1 sulfate from the Stepan Company
[7] Sodium Lauryl sulfate from the Stepan Company
[8] Amphosol HCA from the Stepan Company
[9] Genagen KB Liquid from Clariant Corporation
[10] Ninol COMF from the Stepan Company
[11] Mackam LHS from Rhodia
[12] Viscasil 330M from Momentive Performance Materials with a viscosity of 330,000 cSt (centistokes).
[13] BELSIL DM from Wacker Silicones
[14] ZPT from Arch Chemical
[15] Zinc carbonate from the Bruggeman Group
[16] CO-1895 from Procter & Gamble
[17] CO-1695 from Procter & Gamble
[18] EGDS from Golschmidt Chemical Company
[19] Kathon CG from Akzo Nobel Comparative Data Experiment I In experiment I, the compositions in the below table are compared in relation to their squeeze flow viscosity of the coacervate particles, floc size of the coacervate particles, on-scalp deposition of anti-dandruff active, and consumer acceptance rating. Compositions 1, 3 to 8, and 10 are from the table in the above Examples section. The results are shown in the below table:

|  | Composition | | | | |
| --- | --- | --- | --- | --- | --- |
|  | 1# | 3# | 4# | 5# | 6# |
| (a) + (b) | Total of 0.345% | Total of 0.3% | Total of 0.3% | Total of 0.36% | Total of 0.36% |
| (a):(b) | 6.67:1 ratio | 9:1 ratio | 9:1 ratio | 3:1 ratio | 3:1 ratio |
| Amount of (a) | 0.3%[1] | 0.27%[1] | 0.27%[1] | 0.27%[1] | 0.27%[1] |
| Amount of (b) | 0.045%[2] | 0.03%[2] | 0.03%[2] | 0.09%[2] | 0.09%[2] |
| Squeeze flow viscosity of coacervate particles @ 100 s$^{-1}$ | 35.0 | 57.0 | 56.7 | 67.6 | 62.8 |
| % coacervate particles with a floc size of >20 microns | 6.0 | 14.7 | 14.0 | 12.5 | 9.4 |
| On-scalp deposition of anti-dandruff active (microgram/cm$^2$) | 3.5 | — | 1.4 | — | 2.2 |
| Mean consumer acceptance rating and conclusion (on scale of 1 to 100) | 80 | 70 | 60 | 50 | 40 |
| Representation on The FIGURE | White-filled circle | White-filled circle | White-filled circle | Dark grey-filled circle | Dark grey-filled circle |

KEY:
[1] = guar hydroxypropyltrimonium chloride (charge density of 0.8 meq/g and M.Wt. of 500,000 g/mol);
[2] = PQ-76 from Rhodia (charge density of 1.6 meq/g and M.Wt. of 1,000,000 g/mol).

|  | Composition | | | |
| --- | --- | --- | --- | --- |
|  | 7# | X | 10# | 8# |
| (a) + (b) | Total of 0.55% | Total of 0.4% (no [b] present) | Total of 0.6% | Total of 0.25% |
| (a):(b) | 1.2:1 ratio | 0.4:0 ratio | 19:1 ratio | 19:1 ratio |
| Amount of (a) | 0.3%[1] | 0.4%[1] | 0.57%[3] | 0.24%[3] |
| Amount of (b) | 0.25%[2] | — | 0.03%[3] | 0.01%[3] |
| Squeeze flow viscosity of coacervate particles at 100 s$^{-1}$ | 78.3 | 10.56 | 28.89 | 30.04 |
| % coacervate particles with a floc size of >20 microns | 12.5 | 3.95 | 45.85 | 18.65 |
| On-scalp deposition of anti-dandruff active (microgram/cm$^2$) | 4.6 | 1 | 2.9 | 3.1 |
| Zinc carbonate deposition on scalp (microgram/cm$^2$) | — | 2.5 | 8.7 | 9.92 |
| Mean consumer acceptance rating and conclusion (on scale of 1 to 100) | 20 | 80 | 40 | 80 |
| Representation on The FIGURE | Dark grey-filled circle | White-filled circle | Light grey-filled circle | White-filled circle |

KEY:
# = from the above Examples section;
[1] = guar hydroxypropyltrimonium chloride (charge density of 0.7 meq/g and M.Wt. of 425,000 g/mol);
[2] = PQ-76 from Rhodia (charge density of 1.6 meq/g and M.Wt. of 1,000,000 g/mol);
[3] = a blend from Ashland, which is a blend of 95:5 guar hydroxypropyltrimonium chloride (M.Wt. 500,000 g/mol; charge density 1.1 meq/g) to AM/APTAC (M.Wt. 1.1 million g/mol; charge density 1.8 meq/g).

The compositions detailed in the Examples section above comprise various ratios of guar hydroxypropyltrimonium chloride and PQ-76. Experiment I shows the trade-off that exists between better consumer feel rating and increased on-scalp anti-dandruff deposition. Composition X is a guar only control.

The (a)+(b) value pursuant to the present invention correlates with regard to consumer acceptance. This can be seen when Compositions 8 and 10 are compared. Composition 10 is a high depositor that results in an unacceptable mean consumer acceptance rating. Composition 8, on the other hand, is high depositor that has a good consumer acceptance rating. Compositions 8 and 10 differ only in the total amount of cationic guar polymer plus cationic copolymer i.e. the (a)+(b) value. The anti-dandruff deposition for both compositions 8 and 10 are similar. The proportion of the coacervate particles with a floc size of greater than 20 microns is smaller for composition 8 versus composition 10, which due to the floc size results in composition 8 having a good consumer acceptance rating and composition 10 a bad consumer acceptance rating.

Experiment II:

Compositions A to H below are prepared. The compositions A to H are based on a chassis comprising 12.5% (SLE1S); 1.5% sodium lauryl sulfate (SLS); 1.5% Cocamidopropyl betaine (CAPB); 1% dimethiconol emulsion from Wacker. Compositions B and C are pursuant to the present invention. Compositions A, D, E, F, G and H are not pursuant to the present invention. Composition A is representative of Example 1 of EP1080714A2, particularly with regard to the cationic guar polymer and the cationic copolymer. The chassis is analogous to the other components of Example 1 of EP1080714A2. The US equivalent of EP1080714A2 is US2003/0176303. The compositions in the below table are compared in relation to the squeeze flow viscosity of the coacervate particles, floc size of the coacervate particles, on-scalp deposition of anti-dandruff active. The results are shown in the table.

been replaced with a cationic copolymer that falls within the definition of cationic copolymer (b) pursuant to the present invention. In composition E, the cationic guar of composition A has been replaced with a cationic guar that falls within the definition of cationic guar (a) pursuant to the present invention. However, compositions D and E still result in coacervate properties that fall outside the scope of the present invention vis-à-vis squeeze flow viscosity and floc size. Composition F, G, and H demonstrate a ratio of (a):(b) falling within the scope of the present invention, but do not comprise cationic guar polymer or cationic copolymer molecular weights and/or charge density values that fall within the scope of the present invention. This results in coacervate properties of floc size and squeeze flow viscosity that fall outside the present invention. The relationship between coacervate properties of floc size and squeeze flow viscosity of coacervate and consumer acceptance are explained in the section on the FIGURE.

THE FIGURE

The FIGURE is a graph that relates the coacervate properties of floc size, squeeze flow viscosity and consumer acceptance. Axis X: Coacervate squeeze flow viscosity in centipoise at 100 $s^{-1}$. Axis Y: percentage of coacervate particles with a floc size of greater than about 20 microns. The bubble size relates to consumer acceptance rating (larger bubbles equates to greater consumer acceptance).

| | Composition | | | | | | | |
|---|---|---|---|---|---|---|---|---|
| | A | B | C | D | E | F | G | H |
| Salcare SC60* | 0.08 | — | — | — | 0.08 | 0.045 | 0.045 | — |
| Jaguar C17§ | 0.15 | — | — | 0.15 | — | 0.3 | — | 0.3 |
| AM:Triquat (b)[2] | — | 0.045 | — | 0.08 | — | — | — | 0.045 |
| guar/AM/APTAC[3] (Blend of (a) and (b)). | — | — | 0.4 | — | — | — | — | — |
| Jaguar C500 (a)[1] | — | 0.3 | — | — | 0.15 | — | 0.3 | — |
| Ratio of (a):(b) | 1.875:1 | 6.67:1 | 19:1 | 1.875:1 | 1.875:2 | 6.67:1 | 6.67:1 | 6.67:1 |
| % coacervate particles with a floc size of >20 microns | 74.6 | 6.0 | 18.7 | 69.0 | 14.8 | 46.8 | 12.4 | 55.0 |
| Squeeze flow viscosity of coacervate particles @100 $s^{-1}$ | 78.7 | 35.0 | 30.0 | 92.4 | 53.6 | 124.3 | 49.3 | 179.5 |

KEY:
*= Acrylamidopropyltrimonium Chloride/Acrylamide Copolymer with a M.Wt. of 4 million g/mol and a charge density of 4.2 meq/g and is available from Ciba;
§= Jaguar ® C-17 conforms to Formula G above, has a cationic charge density of about 0.6 meq/g and a M.Wt. of about 2.2 million g/mol and is available from Rhodia Company.;
[1] = guar hydroxypropyltrimonium chloride (charge density of 0.7 meq/g and M.Wt. of 425,000 g/mol);
[2] = PQ-76 from Rhodia (charge density of 1.6 meq/g and M.Wt. of 1,000,000 g/mol);
[3] = a blend from Ashland, which is a blend of 95:5 guar hydroxypropyl trimonium chloride (M.Wt. 500,000 g/mol; charge density 1.1 meq/g) to AM/APTAC (M.Wt. 1.1 million g/mol; charge density 1.8 meq/g).

As demonstrated in experiment II, the compositions pursuant to the present invention, B and C, show excellent floc size and squeeze flow viscosity of coacervate and would result in excellent consumer acceptance rating. The compositions A, D, E, F, G and H fall outside the scope of the present invention for the floc size and squeeze flow viscosity of coacervate and would not be well accepted by consumers. Composition A shows a composition where the molecular weight and charge density of both the cationic guar polymer and the cationic copolymer as well as the ratio of (a):(b) are not pursuant to the present invention resulting in floc size and squeeze flow viscosity properties of the coacervate not falling within the scope of the present invention. In composition D, the cationic copolymer of composition A has The bubble size diminishes as floc size or squeeze flow viscosity of the coacervate particles increases, indicating a relationship between consumer acceptance rating and coacervate properties. Floc size or squeeze flow viscosity of the coacervate particles becomes less consumer acceptable when the properties of the cationic polymers are altered, in particular altering their ratio and level outside the scope of the present invention. For example, the dark grey filled circles fall outside the desired consumer acceptance by having cationic guar polymer:cationic copolymer ratios (i.e. (a):(b)) that do not fall within the scope of "wherein the weight ratio of (a):(b) is from about 1000:1 to about 3.5:1". The black filled circle composition falls outside the present invention because the ratio of (a):(b) falls below the scope of "wherein the weight ratio of (a):(b) is from about 1000:1 to about 3.5:1". The light grey filled circle falls outside the desired consumer acceptance by exceeding the "wherein the sum of (a)+(b) is an amount of from about 0.0001% to about 0.7%".

Clauses

The following clauses are part of the description.

1. A hair conditioning composition comprising:
   (a) a cationic guar polymer, wherein the cationic guar polymer has a weight average molecular weight of less than about 1 million g/mol, and wherein the cationic guar polymer has a charge density of from about 0.1 meq/g to about 2.5 meq/g;
   (b) a cationic copolymer of an acrylamide monomer and a cationic monomer, wherein the copolymer has a charge density of from about 1.0 meq/g to about 3.0 meq/g;
   (c) an anti-dandruff active;
   (d) a cosmetically acceptable carrier;
   (e) a surfactant;
   wherein the weight ratio of (a):(b) is from about 1000:1 to about 3.5:1;
   and wherein the sum of (a)+(b) is an amount of from about 0.0001% to about 0,7%, by total weight of the composition.
2. The composition according to clause 1, wherein cationic guar polymer has a weight average molecular weight of from about 150 thousand to about 800 thousand g/mol, or from about 200 thousand to about 700 thousand g/mol, or from about 300 thousand to about 700 thousand g/mol, or from about 400 thousand to about 600 thousand g/mol.
3. The composition according to any of the preceding clauses, wherein the weight ratio of (a):(b) is from about 800:1 to about 4:1, or from about 500:1 to about 4:1, or from about 100:1 to about 5:1, or from about 100:1 to about 6:1, or from about 50:1 to about 6.5:1, or from about 50:1 to about 7:1, or from about 50:1 to about 8.3:1, or from about 50:1 to about 16.7:1.
4. The composition according to any of the preceding clauses, wherein the cationic copolymer has a charge density of from about 1.1 meq/g to about 2.5 meq/g, or from about 1.1 meq/g to about 2.3 meq/g, or from about 1.2 meq/g to about 2.2 meq/g, or from about 1.2 meq/g to about 2.1 meq/g, or from about 1.3 meq/g to about 2.0 meq/g, or from about 1.3 meq/g to about 1.9 meq/g.
5. The composition according to any of the preceding clauses, wherein the composition comprises a zinc-containing layered material, wherein the zinc-containing layered material is selected from the group consisting of basic zinc carbonate, zinc carbonate hydroxide, hydrozincite, zinc copper carbonate hydroxide, aurichalcite, copper zinc carbonate hydroxide, rosasite, phyllosilicate containing zinc ions, layered double hydroxide, hydroxy double salts, and mixtures thereof.
6. The composition according to any of the preceding clauses, wherein the on-scalp deposition of basic zinc carbonate is at least about 1 microgram/cm$^2$.
7. The composition according to any of the preceding clauses, wherein the cosmetically acceptable carrier is a cosmetically acceptable aqueous carrier and is present at a level of from about 20% to about 95%, or from about 60% to about 85%.
8. The composition according to any of the preceding clauses, wherein the sum of (a)+(b) is from about 0.01% to about 0.7%, or from about 0.1% to about 0.5%, or from about 0.1% to about 0.4%, or from about 0.2% to about 0.3%, by total weight of the composition.
9. The composition according to any of the preceding clauses, wherein the composition comprises from about 0.01% to about 0.7%, or from about 0.04% to about 0.55%, or from about 0.08% to about 0.5%, or from about 0.16% to about 0.5%, or from about 0.2% to about 0.5%, or from about 0.3% to about 0.5%, or from about 0.4% to about 0.5%, cationic guar polymer (a), by total weight of the composition.
10. The composition according to any of the preceding clauses, wherein the composition comprises from about 0.001% to about 0.1%, or from about 0.01% to about 0.1%, from about 0.02% to about 0.1%, cationic copolymer (b), by total weight of the composition.
11. The composition according to any of the preceding clauses, wherein the composition has a viscosity of 4,000 cP to 20,000 cP, measured at 26.6° C. with a Brookfield R/S Plus Rheometer at 2 s$^{-1}$.
12. The composition according to any of the preceding clauses, wherein the surfactant is an anionic surfactant.
13. The composition according to any of the preceding clauses, wherein the cationic monomer is selected from the group consisting of dimethylaminoethyl (meth) acrylate, dimethylaminopropyl (meth)acrylate, ditertiobutylaminoethyl (meth)acrylate, dimethylaminomethyl (meth)acrylamide, dimethylaminopropyl (meth) acrylamide; ethylenimine, vinylamine, 2-vinylpyridine, 4-vinylpyridine; trimethylammonium ethyl (meth)acrylate chloride, trimethylammonium ethyl (meth)acrylate methyl sulphate, dimethylammonium ethyl (meth)acrylate benzyl chloride, 4-benzoyl-benzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, and mixtures thereof.
14. Use of the composition, according to any of clauses 1 to 11, for treating hair.
15. The use, according to clause 12, for achieving improved hair feel.
16. A method for treating hair comprising applying to hair a composition according to any of clauses 1 to 12.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. Method of achieving improved hair feel, comprising applying to hair a composition comprising:
   (a) a cationic guar polymer, wherein the cationic guar polymer has a weight average molecular weight of 800,000 g/mol or less, and wherein the cationic guar polymer has a charge density of from about 0.1 meq/g to about 2.5 meq/g;
   (b) a cationic copolymer of an acrylamide monomer and a cationic monomer, wherein the acrylaminde monomer has a following Formula AM:

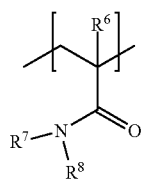

where $R^6$ is H or $C_{1-4}$ alkyl; and $R^7$ and $R^8$ are independently selected from the group consisting of H, $C_{1-4}$ alkyl, $CH_2OCH_3$, $CH_2OCH_2CH(CH_3)_2$, and phenyl, or together are $C_{3-6}$cycloalkyl; and
the cationic monomer is selected from one of the following:

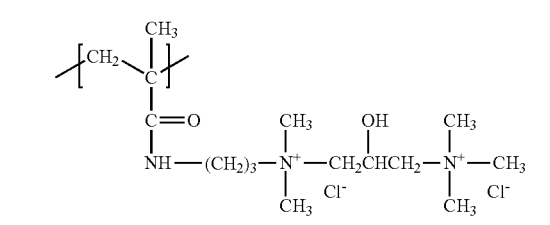

I)

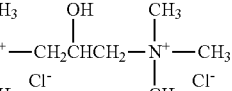

II)

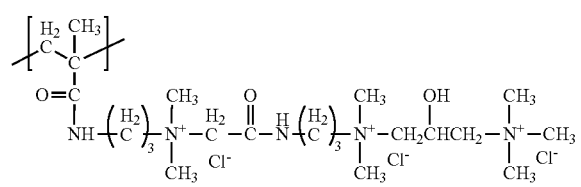

and III)

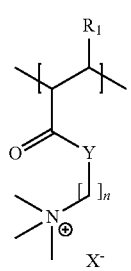

where R1 = ——H or ——$CH_3$
where Y = ——O—— or ——NH
where n = ——$CH_2$——, ——$CH_2CH_2$——, ——$CH_2CH_2CH_2$——, or ——$CH_2CH_2CH_2CH_2$——
where X = Cl, $CH_3SO_4$;

wherein the copolymer has a charge density of from about 1.0 meq/g to about 3.0 meq/g;
   (c) an anti-dandruff active;
   (d) a cosmetically acceptable carrier;
   (e) a surfactant;
   wherein the weight ratio of (a):(b) is from about 100:1 to about 6:1;
   and wherein the sum of (a)+(b) is an amount of from about 0.1% to about 0.5%, by total weight of the composition;
   wherein the composition forms coacervate particles upon dilution of the composition with water;
   and wherein the coacervate particles have a squeeze flow viscosity of from about 1 Pa·s to about 100 Pa·s;
   and wherein the percentage of coacervate particles with a floc size of greater than about 20 micron is from about 1% to about 60%;
   and wherein the on-scalp deposition of the anti-dandruff active is at least about 1microgram/cm$^2$.

2. The method according to claim 1, wherein a mean consumer acceptance rating, on a scale of 1 to 100, of 60 or more is achieved.

3. The method according to claim 1, wherein cationic guar polymer has a weight average molecular weight of from about 150 thousand to less than 800 thousand g/mol.

4. The method according to claim 1, wherein cationic guar polymer has a weight average molecular weight of from about 200 thousand to about 700 thousand g/mol.

5. The method according to claim 1, wherein the weight ratio of (a):(b) is from about 50:1 to about 8.3:1.

6. The method according to claim 1, wherein the cationic copolymer has a charge density of from about 1.1 meq/g to about 2.5 meq/g.

7. The method according to claim 1, wherein the cationic copolymer has a charge density of from about 1.2 meq/g to about 2.2 meq/g.

8. The method according to claim 1, wherein the anti-dandruff active is selected from the group consisting of antimicrobial actives, pyridinethione salts, azoles, selenium sulfide, particulate sulfur, keratolytic acid, salicylic acid, octopirox (piroctone olamine), coal tar, and mixtures thereof.

9. The method according to claim 1, wherein the composition comprises a zinc-containing layered material, wherein the zinc-containing layered material is selected from the group consisting of basic zinc carbonate, zinc carbonate hydroxide, hydrozincite, zinc copper carbonate hydroxide, aurichalcite, copper zinc carbonate hydroxide, rosasite, phyllosilicate containing zinc ions, layered double hydroxide, hydroxy double salts, and mixtures thereof.

10. The method according to claim 9, wherein the on-scalp deposition of the basic zinc carbonate is at least about 1 microgram/cm$^2$.

11. The method according to claim 1, wherein the cosmetically acceptable carrier is a cosmetically acceptable aqueous carrier and is present at a level of from about 20% to about 95%.

12. The method according to claim 1, wherein the composition comprises from about 0.01% to about 0.5% cationic guar polymer (a), by total weight of the composition.

13. The method according to claim 1, wherein the composition comprises from about 0.001% to about 0.1% cationic copolymer (b), by total weight of the composition.

14. The method according to claim 1, wherein the percentage of coacervate particles with a floc size of greater than about 20 micron is from about 1% to about 40%.

15. The method according to claim 1, wherein the coacervate particles have a squeeze flow viscosity of from about 2 Pa·s to about 60 Pa·s.

16. The method according to claim 1, wherein the surfactant is an anionic surfactant.

17. The method according to claim 14, wherein the composition further comprises a co-surfactant, wherein the co-surfactant is selected from the group consisting of zwitterionic surfactants, amphoteric surfactants, non-ionic surfactants, and mixtures thereof.

* * * * *